US010626115B2

United States Patent
Loge et al.

(10) Patent No.: US 10,626,115 B2
(45) Date of Patent: Apr. 21, 2020

(54) FUSED PYRIMIDINONE AND TRIAZINONE DERIVATIVES CONTAINING BRIDGED NITROGEN, THEIR PROCESS OF PREPARATION AND THEIR THERAPEUTIC USES AS ANTIFUNGAL AND/OR ANTIPARASITIC AGENTS

(71) Applicant: UNIVERSITE DE NANTES, Nantes (FR)

(72) Inventors: Cédric Loge, Nantes (FR); Rémi Guillon, La Roche sur Yon (FR); David Montoir, Pont-Chateau (FR); Fabrice Pagniez, La Chapelle Heulin (FR); Patrice Le Pape, Vertou (FR)

(73) Assignee: UNIVERSITE DE NANTES, Nantes (FR)

( * ) Notice: Subject to any disclaimer, the term of this patent is extended or adjusted under 35 U.S.C. 154(b) by 0 days.

(21) Appl. No.: 15/748,905

(22) PCT Filed: Jul. 22, 2016

(86) PCT No.: PCT/EP2016/067530
§ 371 (c)(1),
(2) Date: Jan. 30, 2018

(87) PCT Pub. No.: WO2017/021178
PCT Pub. Date: Feb. 9, 2017

(65) Prior Publication Data
US 2019/0002467 A1    Jan. 3, 2019

(30) Foreign Application Priority Data
Jul. 31, 2015  (WO) ............... PCT/EP2015/067752

(51) Int. Cl.
C07D 487/04  (2006.01)
A61P 33/02  (2006.01)
A61P 31/10  (2006.01)

(52) U.S. Cl.
CPC ........... *C07D 487/04* (2013.01); *A61P 31/10* (2018.01); *A61P 33/02* (2018.01)

(58) Field of Classification Search
CPC .................................................. C07D 487/04
See application file for complete search history.

(56) References Cited

FOREIGN PATENT DOCUMENTS

| DE | 3542676 A1 | 6/1987 | |
|---|---|---|---|
| EP | 0548553 A2 | 6/1993 | |
| EP | 0667346 A2 | 8/1995 | |
| EP | 0667346 A3 | 1/1998 | |
| WO | 0149700 A1 | 7/2001 | |
| WO | WO 2017020944 * | 2/2017 | ........... C07D 487/04 |

OTHER PUBLICATIONS

Bernandes. Current Medicinal Chemistry, 2013, 20, 2673-96 (Year: 2013).*
Kubir. ISRN Preventive Medicine, 2013, 1-13 (Year: 2013).*
Reithinger. The Lancet, 2007, 7, 581-96 (Year: 2007).*
International Search Report dated Sep. 28, 2016 during the prosecution of PCT/EP2016/067530.
Tasaka et al., "Optically Active Antifungal Azoles. I. Synthesis and Antifungal Activity of (2R,3R)-2-(2,4-Difluorophenyl)-3-mercapto-1-(IH-1,2,4-triazol-1-y 1)-2-butanol and Its Stereoisomers," Chem. Pharm. Bull. 41(6) 1035-1042 (1993).
Cornley, O. A., et al., "Posaconazole vs. Fluconazole or Intraconazole Prophylaxis in Patents with Neutropenia" The New England Journal of Medicine 356(4):348-359 (Jan. 25, 2007).
Dolton, M. J., et al., "Optimizing azole antifungal therapy in teh prophylaxis and treatment of fungal infections" Current Opinion Infectious Diseases 27(6):493-500 (Dec. 2014).
Döring, M., et al., "Comparison of itraconazole, voriconazole, and posaconazole as oral antifungal prophylaxis in pediatric patients following allogeneic hematopoietic stem cell transplantation" Eur J Clin Microbiol Infect Dis 33:629-638 (2014).

* cited by examiner

*Primary Examiner* — Noble E Jarrell
(74) *Attorney, Agent, or Firm* — Troutman Sanders LLP

(57) ABSTRACT

The present invention concerns novel fused pyrimidinone and triazinone derivatives containing bridged nitrogen, their process of preparation and their use as antifungal or antiparasitic agents.

13 Claims, 2 Drawing Sheets

FUSED PYRIMIDINONE AND TRIAZINONE DERIVATIVES CONTAINING BRIDGED NITROGEN, THEIR PROCESS OF PREPARATION AND THEIR THERAPEUTIC USES AS ANTIFUNGAL AND/OR ANTIPARASITIC AGENTS

CROSS-REFERENCE TO RELATED APPLICATIONS

This is a U.S. national phase application under 35 U.S.C. 371 of International Patent Application No. PCT/EP2016/067530, filed Jul. 22, 2016, and claims benefit of priority to PCT/EP2015/067752, filed Jul. 31, 2015. The entire content of this application is hereby incorporated by reference.

FIELD OF TECHNOLOGY

The present invention relates to novel antifungal and/or antiparasitic agents, compositions containing these compounds, use of these compounds in medicine and their process of preparation.

BACKGROUND

Due to their ease of use including administration route and relative inocuity, the azole derivatives (such fluconazole, itraconazole, voriconazole, posaconazole) are widespread antifungal agents. However, their use as first intention has lead to resistance.

Besides azole anti-fungal agents, alternative classes include polyenes such as amphotericine B (Fungizone) and its lipidic forms (Ambizome and Abelcet), as well as the echinocandines (caspofungine, anidulafungine, micafungine). However, these alternative antifungal agents are generally costly and not suitable for oral administration for treating systemic disorders.

Thus, there has been a continued interest in developing antifungal agents in particular agents able to circumvent resistance phenomenons, such as those originating from mutations of the gene coding for their target (14α-demethylase, CYP51) and/or their efflux by pumps of the CDR or MDR pumps.

SUMMARY

It is thus desirable to provide alternative antifungal agents circumventing one or more of these drawbacks, that is overcoming resistance and/or suitable for oral and iv administration.

14α-demethylase is also a therapeutic target for antiprotozoan therapy (Lepesheva et al. Curr Top Med Chem. 2011; 11(16):2060-71), in particular against Trypanosomatidae, such as *Leishmania* for which the available treatments remain unsatisfactory.

It is thus also desirable to provide for alternative improved treatments against these parasites.

Some of these aims and others have been solved by the compounds of the present invention.

The present invention concerns compounds of general formula (I):

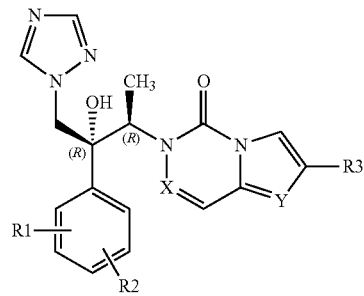

Wherein

X is selected from the group consisting in CH and N;

Y is selected from the group consisting in CH and N;

R1 and R2, identical or different are independently chosen from the group consisting in Halogen atoms;

R3 is selected from the group consisting in

H; (C1-C6)alkyl; CN; COO(C1-C6)alkyl; OH, halogen atoms, O(C1-C6)alkyl, $NO_2$, perhalogeno(C1-C6)alkyl, CO(C1-C6)alkyl, $CONH_2$, CONH(C1-C6)alkyl, CON [(C1-C6)alkyl]$_2$, $(CH_2)_n$NRR'

5 to 10 membered aryl groups optionally substituted by one or more identical or different groups chosen from: halogen atoms, perhalogeno(C1-C6)alkyl, CN, $NO_2$, O(C1-C6)Alkyl, OH, (C1-C6)alkyl, CO(C1-C6)alkyl, COO(C1-C6)alkyl, COOH, CONRR', 5 to 10 membered heteroaryl groups comprising one, two or three heteroatoms chosen from O, N and S;

n is 0 or 1;

R represent a H atom or a group COR";

R' represents a H atom or a group selected from (C1-C6)alkyl,

R" represents a group selected from (C1-C6)alkyl, (C2-C6)alkenyl;

or one of its pharmaceutically acceptable salts.

According to an embodiment, X is CH and Y is N.

According to an embodiment, X is N; and Y is CH.

According to an embodiment, R1 and R2 are located in ortho and para positions of the phenyl ring.

According to an embodiment, R1 and R2, identical or different are independently chosen from Halogen atoms, more particularly fluorine atoms.

According to an embodiment, R3 is selected from the group consisting in 5 to 10 membered aryl groups optionally substituted by one or more identical or different groups chosen from: halogen atoms, perhalogeno(C1-C6)alkyl, CN, $NO_2$, O(C1-C6)Alkyl, and 5 to 10 membered heteroaryl groups comprising one, two or three heteroatoms chosen from O, N and S.

According to an embodiment, R3 is selected from the group consisting in 5 to 10 membered aryl groups substituted by one or more identical or different groups chosen from: halogen atoms, perhalogeno(C1-C6)alkyl, CN, $NO_2$, O(C1-C6)Alkyl; more particularly substituted by CN, $NO_2$, O(C1-C6)Alkyl.

According to an embodiment, compounds of formula (I) are of formula (Ia):

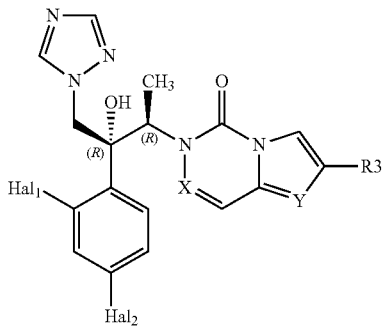

(Ia)

or one of its pharmaceutically acceptable salts,

Where Hal1 and Hal2, identical or different independently represent halogen atoms, more particularly fluorine atoms, and X, Y and R3 are defined as above.

Unless specified otherwise, the terms used hereabove or hereafter have the meaning ascribed to them below:

"Halo", "hal" or "halogen" refers to fluorine, chlorine, bromine or iodine atom.

"Alkyl" represents an aliphatic-hydrocarbon group which may be straight or branched having 1 to 20 carbon atoms in the chain unless specified otherwise. Preferred alkyl groups have 1 to 12 carbon atoms, more preferably have 1 to 8 carbon atoms in the chain, most preferably have 1 to 6 carbon atoms in the chain. In a particularly preferred embodiment the alkyl group has 1 to 4 carbon atoms in the chain. Exemplary alkyl groups include methyl, ethyl, n-propyl, iso-propyl, iso-butyl, n-butyl, tert-butyl, n-pentyl, 3-pentyl, octyl, nonyl, decyl.

"Alkenyl" refers to a straight or branched hydrocarbon chain containing from 2 to 8, preferably 2 to 20, preferably 2 to 6, and still more preferably 2 to 4 carbon atoms having one or more carbon-carbon double bonds. Examples include ethenyl, propenyl, isopropenyl, 2,4-pentadienyl, etc.

"Aryl" refers to an aromatic monocyclic, bicyclic or tricyclic hydrocarbon ring system of 6 to 14 carbon atoms. More preferably aryl refers to a monocyclic or bicyclic ring containing 6 to 10 carbon atoms. Exemplary aryl groups include phenyl, naphthyl, indenyl, phenanthryl, biphenyl. Most preferably the aryl group is Phenyl.

The term "heteroaryl" refers to a 5 to 14, preferably 5 to 10 membered aromatic mono-, bi- or multicyclic ring wherein at least one member of the ring is a hetero atom such as N, O, S. Examples include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazoyl, tetrazolyl, isoquinolyl, benzothienyl, isobenzofuryl, pyrazolyl, carbazolyl, benzimidazolyl, isoxazolyl.

"Alkyl", "alkenyl", "aryl", etc. . . . also refers to the corresponding divalent "alkylene", "alkenylene", "arylene" etc., which are formed by the removal of two hydrogen atoms.

The compounds of the present invention may possess an acidic group or a basic group which may form corresponding salts. Thus the present invention includes salts of compounds of formula (I). The salts may preferably be pharmaceutically acceptable salts. The acidic group may form salts with bases. The base may be an organic amine base, for example trimethylamine, tert-butylamine, tromethamine, meglumine, epolamine, etc. The acidic group may also form salts with inorganic bases like sodium hydroxide, potassium hydroxide, etc. The basic group may form salts with inorganic acids like hydrochloric acid, sulfuric acid, hydrobromic acid, sulfamic acid, phosphoric acid, nitric acid etc and organic acids like acetic acid, propionic acid, succinic acid, tartaric acid, citric acid, methanesulfonic acid, benzenesulfonic acid, glucoronic acid, glutamic acid, benzoic acid, salicylic acid, toluenesulfonic acid, oxalic acid, fumaric acid, maleic acid etc. Further, compounds of formula (I) may form quaternary ammonium salts and salts with amino acids such as arginine, lysine, etc. Lists of suitable salts may be found in Remington's Pharmaceutical Sciences, 17th ed., Mack Publishing Company, Easton, Pa., 1985, p. 1418 and P. H. Stahl, C. G. Wermuth, *Handbook of Pharmaceutical salts—Properties, Selection and Use*, Wiley-VCH, 2002, the disclosures of which are hereby incorporated by reference.

As used herein, the term "patient" refers to a warm-blooded animal such as a mammal, preferably a human or a human child, which is afflicted with, or has the potential to be afflicted with one or more diseases and conditions described herein.

As used herein, a "therapeutically effective amount" refers to an amount of a compound of the present invention which is effective in reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment and chronic use.

As used herein, the expression "pharmaceutically acceptable" refers to those compounds, materials, compositions, or dosage forms which are, within the scope of sound medical judgment, suitable for contact with the tissues of human beings and animals without excessive toxicity, irritation, allergic response, or other complications commensurate with a reasonable benefit/risk ratio.

Following are examples of some of the representative compounds of the invention. These examples are for illustration purposes only and should not be considered to be limiting the invention.

6-[(1R,2R)-2-(2,4-Difluorophenyl)-2-hydroxy-1-methyl-3-(1H-1,2,4-triazol-1-yl)propyl]imidazo[1,2-c]pyrimidin-5-one (27)

6-[(1R,2R)-2-(2,4-Difluorophenyl)-2-hydroxy-1-methyl-3-(1H-1,2,4-triazol-1-yl)propyl]-2-methylimidazo[1,2-c]pyrimidin-5-one (28)

6-[(1R,2R)-2-(2,4-Difluorophenyl)-2-hydroxy-1-methyl-3-(1H-1,2,4-triazol-1-yl)propyl]-2-phenylimidazo[1,2-c]pyrimidin-5-one (29)

6-[(1R,2R)-2-(2,4-Difluorophenyl)-2-hydroxy-1-methyl-3-(1H-1,2,4-triazol-1-yl)propyl]-2-(4-fluorophenyl)imidazo[1,2-c]pyrimidin-5-one (30)

6-[(1R,2R)-2-(2,4-Difluorophenyl)-2-hydroxy-1-methyl-3-(1H-1,2,4-triazol-1-yl)propyl]-2-(4-chlorophenyl)imidazo[1,2-c]pyrimidin-5-one (31)

6-[(1R,2R)-2-(2,4-Difluorophenyl)-2-hydroxy-1-methyl-3-(1H-1,2,4-triazol-1-yl)propyl]-2-(4-bromophenyl)imidazo[1,2-c]pyrimidin-5-one (32)

6-[(1R,2R)-2-(2,4-Difluorophenyl)-2-hydroxy-1-methyl-3-(1H-1,2,4-triazol-1-yl)propyl]-2-[(4-trifluoromethyl)phenyl]imidazo[1,2-c]pyrimidin-5-one (33)

6-[(1R,2R)-2-(2,4-Difluorophenyl)-2-hydroxy-1-methyl-3-(1H-1,2,4-triazol-1-yl)propyl]-2-(4-cyanophenyl)imidazo[1,2-c]pyrimidin-5-one (34)

6-[(1R,2R)-2-(2,4-Difluorophenyl)-2-hydroxy-1-methyl-3-(1H-1,2,4-triazol-1-yl)propyl]-2-(4-nitrophenyl)imidazo[1,2-c]pyrimidin-5-one (35)

6-[(1R,2R)-2-(2,4-Difluorophenyl)-2-hydroxy-1-methyl-3-(1H-1,2,4-triazol-1-yl)propyl]-2-(thiazol-2-yl)imidazo[1,2-c]pyrimidin-5-one (36)

Ethyl-6-[(1R,2R)-2-(2,4-difluorophenyl)-2-hydroxy-1-methyl-3-(1H-1,2,4-triazol-1-yl)propyl]-5-oxo-imidazo[1,2-c]pyrimidine-2-carboxylate (37)

6-[(1R,2R)-2-(2,4-Difluorophenyl)-2-hydroxy-1-methyl-3-(1H-1,2,4-triazol-1-yl)propyl]-5-oxo-imidazo[1,2-c]pyrimidine-2-carbonitrile (38)

3-[(1R,2R)-2-(2,4-Difluorophenyl)-2-hydroxy-1-methyl-3-(1,2,4-triazol-1-yl)propyl]-3H-pyrrolo[1,2-d][1,2,4]triazin-4-one (44)

7-Bromo-3-[(1R,2R)-2-(2,4-difluorophenyl)-2-hydroxy-1-methyl-3-(1,2,4-triazol-1-yl)propyl]-3H-pyrrolo[1,2-d][1,2,4]triazin-4-one (45)

3-[(1R,2R)-2-(2,4-Difluorophenyl)-2-hydroxy-1-methyl-3-(1,2,4-triazol-1-yl)propyl]-4-oxo-3,4-dihydro-pyrrolo[1,2-d][1,2,4]triazine-7-carbonitrile (46)

3-[(1R,2R)-2-(2,4-Difluorophenyl)-2-hydroxy-1-methyl-3-(1,2,4-triazol-1-yl)propyl]-7-phenyl-3H-pyrrolo[1,2-d][1,2,4]triazin-4-one (47)

7-(4-Chlorophenyl)-3-[(1R,2R)-2-(2,4-difluorophenyl)-2-hydroxy-1-methyl-3-(1,2,4-triazol-1-yl)propyl]-3H-pyrrolo[1,2-d][1,2,4]triazin-4-one (48)

4-{3-[(1R,2R)-2-(2,4-Difluorophenyl)-2-hydroxy-1-methyl-3-(1,2,4-triazol-1-yl)propyl]-4-oxo-3,4-dihydro-pyrrolo[1,2-d][1,2,4]triazin-7-yl}benzonitrile (49)

3-[(1R,2R)-2-(2,4-Difluorophenyl)-2-hydroxy-1-methyl-3-(1,2,4-triazol-1-yl)propyl]-7-(4-nitrophenyl)-3H-pyrrolo[1,2-d][1,2,4]triazin-4-one (50)

3-[(1R,2R)-2-(2,4-Difluorophenyl)-2-hydroxy-1-methyl-3-(1,2,4-triazol-1-yl)propyl]-7-(4-methoxyphenyl)-3H-pyrrolo[1,2-d][1,2,4]triazin-4-one (51)

or one of its pharmaceutically acceptable salts.

According to a further object, the present invention also concerns the process of preparation of the compound of formula (I).

The compounds and process of the present invention may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art.

In particular, such methods can be found in R. C. Larock, *Comprehensive Organic Transformations*, VCH publishers, 1989

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Synthesis*, John Wiley and Sons, 1991; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethyl-formamide; alcohols such as ethanol and methanol and ethers, such as diethyl ether and tetrahydrofuran.

The reactions can take place over a wide range of temperatures. In general, we find it convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well-known techniques, such as recrystallization, reprecipitation or the various chromatography techniques, notably column chromatography or preparative thin layer chromatography.

In particular, the compounds of the present invention may be prepared from the processes described below. The intermediates used in the processes are either commercially available or may be synthesized by application or adaptation of well-known starting materials and processes.

According to a first embodiment, the process of preparation of a compound of formula (I) comprises the step of coupling a compound of formula (II) with a compound of formula (III):

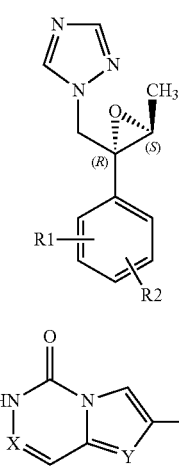

(II)

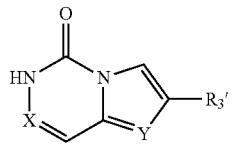

(III)

Where R1, R2, X and Y are defined as in formula (I) and R3' is a R3 group that may be further converted into an alternative desired R3 group;

optionally followed by converting the compound so obtained by the coupling of compounds (II) and (III) into a compound (I) with the desired R3 group.

The coupling reaction may be carried out in a suitable solvent in the presence of a base. Generally, the reaction may be conducted between room temperature and the reflux temperature of the reaction mixture, typically up to 80° C.

Suitable solvents comprise polar and aprotic solvents, such as N-methyl-2-pyrrolidone (NMP).

Bases include organic or inorganic bases, and include amines (trimethylamine, tert-butylamine . . . ), sodium hydroxide, potassium hydroxide, carbonates, such as potassium carbonate.

The optional conversion reaction may be in particular carried out when compounds of formula (III) with the desired R3 group may not be available or suitable for conducting the coupling reaction. Generally, compounds where R3=R3'=H or halogen atoms may be obtained from the coupling reaction without further conversion.

When needed, the optional conversion reaction generally comprises converting the compound of formula (I) obtained after the coupling reaction where R3' represents a good leaving group, such as a halogen atom into an alternative compound of formula (I) with an alternative desired R3 group, including CN, optionally substituted aryl, heteroaryl.

Generally, this conversion reaction may be conducted by application or adaptation of known methods. For illustration purposes, compounds (I) where R3 represents a CN group may be obtained by converting the compound (I) obtained after the coupling reaction where R3'=Br, by reacting it with $ZN(CN)_2$ in a Paladium catalyzed coupling reaction, in particular in the presence of $Pd(PPh)_3$ in a suitable solvent, such as DMF.

According to another illustrative embodiment, compounds (I) where R3 represents an optionally substituted aryl group may be obtained by converting the compound (I) obtained after the coupling reaction where R3'=Br, by reacting it with the suitable Ar—$B(OH)_2$ reagent where Ar represents the corresponding optionally substituted aryl group. This conversion is generally a Palladium catalyzed coupling reaction, conducted in particular in the presence of $Pd(PPh)_3$ and a base, such as a carbonate (e.g. sodium carbonate) in a suitable solvent such as acetontrile.

The conversion reaction may be carried out at a temperature comprised between the room temperature and the reflux temperature of the reaction mixture, typically up to 120° C. approximately.

The compound (II) may be prepared by application or adaptation of the method reported by A. Tasaka, N. Tamura, Y. Matsushita, K. Teranishi, R. Hayashi, K. Okonogi, K. Itoh, Optically active antifungal azoles. I. Synthesis and antifungal activity of (2R,3R)-2-(2,4-difluorophenyl)-3-mercapto-1-(1H-1,2,4-triazol-1-yl)-2-butanol and its stereoisomers, *Chem. Pharm. Bull.,* 1993, 41 (6), 1035-1041.

The compound of formula (III) may be obtained by a process comprising either of the two alternative embodiments.

According to a first embodiment, the compound (III) may be obtained by a process comprising the step of reacting a compound (IV) with a compound (V):

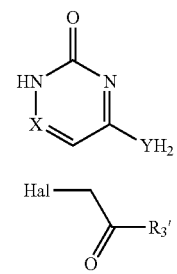

(IV)

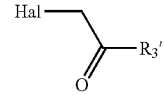

(V)

Where X, Y and R3' are defined as above and Hal represents a halogen atom such as Br or Cl.

This first embodiment is generally used when X is CH and Y is N.

This reaction may be conducted in a suitable solvent such as DMF or methanol, at a temperature comprised between room temperature and the reflux temperature of the reaction mixture, typically up to 70° C. approximately.

According to a second embodiment, the compound of formula (III) may be obtained from a compound of formula (VI)

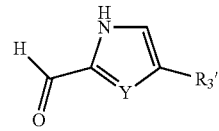

(VI)

This second embodiment is generally used when Y is CH and X is N and R3' is Br.

In this instance, the compound (III) is obtained by coupling the compound (VI) above with ethylcarbazate ($H_2NNHCOOEt$) followed by the addition of a base, such as sodium hydride.

The compound of formula (VI) may be obtained from a compound of formula (VII):

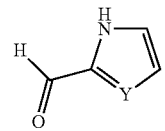

(VII)

This reaction is generally carried out by reacting the compound (VII) with N-bromosuccinimide in a suitable solvent such as acetonitrile.

The compound of formula (VII) may be in turn obtained by reacting a compound of formula (VIII):

(VIII)

with phosphorus oxy chloride (POCl$_3$) in DMF and 1,2-dichloroethane.

The process of the invention may also include the additional step of isolating the obtained compounds.

The salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two and such methods are within the level of a skilled person.

The compounds of the present invention may be useful for the treatment and/or prevention of various diseases and/or disorders, such as fungal conditions and disorders, such as fungal infections, as well as parasitic conditions and disorders such as trypanosomiasis or leishmaniasis According to another object, the present invention concerns pharmaceutical compositions comprising a compound of formula (I) with at least one pharmaceutically acceptable excipient.

According to a still further object, the present invention thus also concerns compounds of formula (I) as defined above for use in treating and/or preventing fungal infections.

According to another embodiment, the present invention concerns the use of a compound of formula (I) for the preparation of a composition for treating and/or preventing fungal infections.

According to a still other embodiment, the present invention concerns the method for treating and/or preventing fungal infections comprising administering a compound of formula (I) to a patient in the need thereof.

Fungal infections include in particular ringworms, onychomycosis, athlete's foot, Jock itch, candidiasis such as candidiasis *Albicans*, cryptococcosis and all infections by other opportunistic organisms such as systemic infections (aspergillosis, zygomycosis . . . ).

The compounds of the present invention may be used in combination with other antifungal agents such as flucytosine, polyenes, echinocandines, antifungal peptides. Said combinations are another object of the present invention.

According to a still further object, the present invention thus also concerns compounds of formula (I) as defined above for use in treating and/or preventing parasitic infectious diseases due to Trypanosomatidae, such as leishmaniasis or trypanosomiasis Trypanosomiasis include African trypanosomiasis (Sleeping Sickness, caused by *Trypanosoma brucei*), South American trypanosomiasis (Chagas Disease, caused by *Trypanosoma cruzi*). Leishmaniasis include cutaneous, mucocutaneous and visceral leishmaniasis caused by various species of *Leishmania*.

According to another embodiment, the present invention concerns the use of a compound of formula (I) for the preparation of a composition for treating and/or preventing parasitic infectious diseases due to Trypanosomatidae, such as leishmaniasis or trypanosomiasis.

According to a still other embodiment, the present invention concerns the method for treating and/or preventing parasitic infectious diseases due to Trypanosomatidae, such as leishmaniasis or trypanosomiasis comprising administering a compound of formula (I) to a patient in the need thereof.

The dosage of drug to be administered depends on such variables as the type and extent of progression of the disease or disorder, the overall health status of the particular patient, the relative biological efficacy of the compound selected, and formulation of the compound, excipients, and its route of administration.

A typical dose range for use according to the invention may be from 1 µg/kg to 1 g/kg of body weight per day. A preferred dose range may be from 3 µg/kg to 1 mg/kg of body weight per day.

The compounds of present invention may be formulated into a pharmaceutically acceptable preparation, on admixing with a carrier, excipient or a diluent, in particular for oral and/or parenteral use. In particular, the compounds of the invention are unexpectedly suitable for oral and/or iv routes of administration, for local and/or systemic treatment.

Preparations for oral administration may be in the form of tablets, capsules or parenterals. A solid carrier can include one or more substances which may also act as flavoring agents, lubricants, solubilizers, suspending agents, fillers, glidants, compression aids, binders or tablet-disintegrating agents; it can also be an encapsulating material. Liquid carriers can include water, an organic solvent, a mixture of both or pharmaceutically acceptable oils and fats. The compositions may conveniently be administered in unit dosage form and may be prepared by any of the methods well known in the pharmaceutical art, for example, as described in Remington: The Science and Practice of Pharmacy, 20th ed.; Gennaro, A. R., Ed.; Lippincott Williams & Wilkins: Philadelphia, Pa., 2000. Pharmaceutically compatible binding agents and/or adjuvant materials can be included as part of the composition.

The tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal.

Preferred tablets contain lactose, cornstarch, magnesium silicate, croscarmellose sodium, povidone, magnesium stearate, or talc in any combination Liquid preparations for parenteral administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, acrylate copolymers, vegetable oils such as olive oil, and organic esters such as ethyl oleate. Aqueous carriers include mixtures of alcohols and water, hydrogels, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, poly oxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate. Formulations for topical application to the skin preferably take the form of dry powder, ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

Alternative administrations include also solutions, ointments or other formulations acceptable for ocular administration.

Other features of the invention will become apparent in the course of the following description of exemplary embodiments that are given for illustration of the invention and not intended to be limiting thereof.

The above mentioned features of the invention are given for illustration of the invention and not intended to be limiting thereof.

FIGURES

FIGS. 1 and 2 represent the survival rate of swiss mice following inoculation with the CAAL93 strain and administration of compounds 29, 34, 35 and 51 respectively.

FIGS. 3 and 4 represent the fungal load in kidney of swiss mice following inoculation with the CAAL93 strain and administration of compounds 29, 34, 35 and 51 respectively.

EXAMPLES

Figure 1:
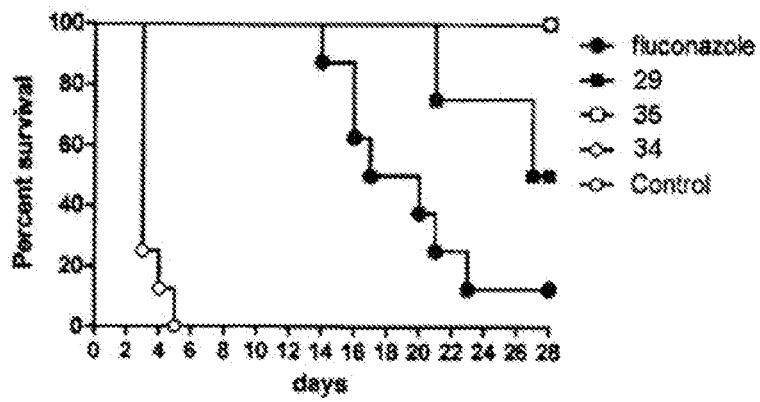

Illustrative compounds of the inventions were prepared according to schemes 1 and 2 below.

Scheme 1.

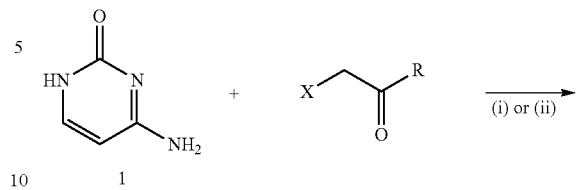

2 X = Cl, R = H
3 X = Cl, R = Me
4 X = Br, R = Ph
5 X = Br, R = 4-F—Ph
6 X = Br, R = 4-Cl—Ph
7 X = Br, R = 4-Br—Ph
8 X = Br, R = 4-CF$_3$—Ph
9 X = Br, R = 4-CN—Ph
10 X = Br, R = 4-NO$_2$—Ph
11 X = Br, R = 2-thiazole
12 X = Br, R = COOEt

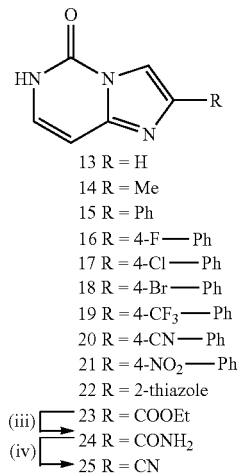

13 R = H
14 R = Me
15 R = Ph
16 R = 4-F—Ph
17 R = 4-Cl—Ph
18 R = 4-Br—Ph
19 R = 4-CF$_3$—Ph
20 R = 4-CN—Ph
21 R = 4-NO$_2$—Ph
22 R = 2-thiazole
(iii) 23 R = COOEt
(iv) 24 R = CONH$_2$
25 R = CN Reagents and conditions: (i) ClCH$_2$COR, DMF, 70° C., 16 h; (ii) BrCH$_2$COR, MeOH, 70° C., 3-42 h; (iii) NH$_4$OH (20%), 80° C., 3 h; (iv) (CF$_3$CO)$_2$O, pyridine, room temperature, 2 h.

Scheme 2.

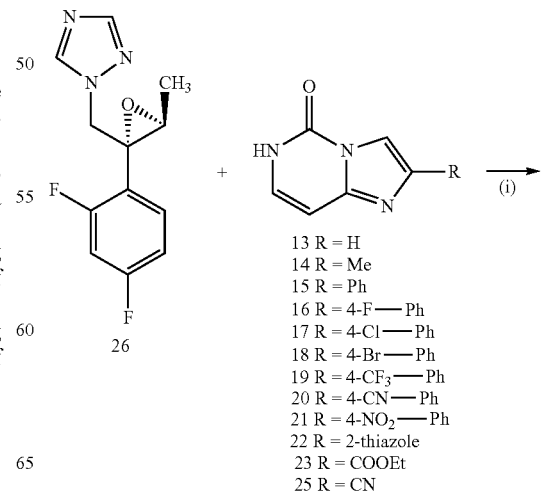

13 R = H
14 R = Me
15 R = Ph
16 R = 4-F—Ph
17 R = 4-Cl—Ph
18 R = 4-Br—Ph
19 R = 4-CF$_3$—Ph
20 R = 4-CN—Ph
21 R = 4-NO$_2$—Ph
22 R = 2-thiazole
23 R = COOEt
25 R = CN -continued

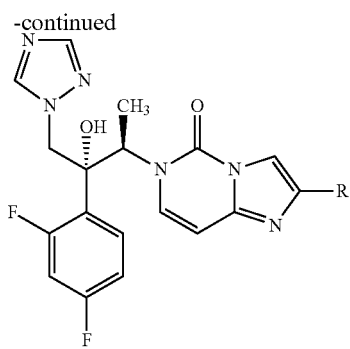

27 R = H
28 R = Me
29 R = Ph
30 R = 4-F—Ph
31 R = 4-Cl—Ph
32 R = 4-Br—Ph
33 R = 4-CF₃—Ph
34 R = 4-CN—Ph
35 R = 4-NO₂—Ph
36 R = 2-thiazole
37 R = COOEt
38 R = CN Reagents and conditions: (i) K₂CO₃, NMP, 80° C., 3 days.

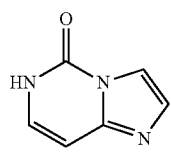

Imidazo[1,2-c]pyrimidin-5-one (13)

To a stirred solution of cytosine 1 (500 mg, 4.50 mmol) in DMF (10 mL) was added chloroacetaldehyde 2 (50% in H₂O) (0.686 mL, 5.40 mmol) and the solution was stirred at 70° C. for 16 h. Solvent was removed under reduced pressure and residue was washed with ethanol and ether to yield compound 13 as a light brown powder (320 mg, 53%): $R_f$=0.47 (EtOAc/MeOH 4:1); mp: 281-282° C.; ¹H NMR (400 MHz, [D₆]DMSO): δ=6.62 (d, 1H, ³J=7.6 Hz), 7.28 (d, 1H, ³J=7.6 Hz), 7.41 (d, 1H, ³J=1.2 Hz), 7.80 (d, 1H, ³J=1.2 Hz), 11.60 ppm (bs, 1H); ¹³C NMR (100 MHz, [D₆]DMSO): δ=97.7, 112.2, 129.4, 132.3, 145.9, 146.4 ppm; IR (KBr): ν=3451, 3121, 3096, 1718, 1630, 1547, 1290, 1252, 1111 cm⁻¹; MS (ESI) m/z 135.8 [M+H]⁺.

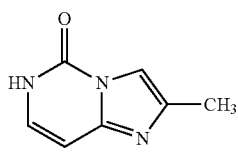

2-Methylimidazo[1,2-c]pyrimidin-5-one (14)

To a stirred solution of cytosine 1 (500 mg, 4.50 mmol) in DMF (10 mL) was added chloroacetone 3 (0.430 mL, 5.40 mmol) and the solution was stirred at 70° C. for 16 h. Solvent was removed under reduced pressure and residue was purified on silica gel column chromatography (methylene chloride/ethanol 97:3 and 95:5) to yield compound 14 as a light brown powder (95 mg, 14%): $R_f$=0.07 (CH₂Cl₂/EtOH 95:5); mp: 299-300° C.; ¹H NMR (400 MHz, [D₆]DMSO): δ=2.27 (s, 3H), 6.51 (d, 1H, ³J=7.2 Hz), 7.22-7.25 (m, 1H), 7.51 (s, 1H), 11.51 ppm (bs, 1H); ¹³C NMR (100 MHz, [D₆]DMSO): δ=14.0, 97.2, 108.3, 129.2, 141.3, 145.5, 146.1 ppm; IR (KBr): ν=3447, 3142, 3091, 1708, 1630, 1404, 1371, 1346, 1300, 1266, 1208, 1176, 783 cm⁻¹; MS (ESI) m/z 149.9 [M+H]⁺.

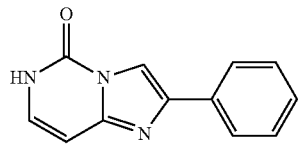 [SMILES: O=c1[nH]ccc2nc(-c3ccccc3)cn12]

2-Phenylimidazo[1,2-c]pyrimidin-5-one (15)

To a stirred solution of cytosine 1 (500 mg, 4.50 mmol) in MeOH (40 mL) was added 2-bromoacetophenone 4 (814 mg, 4.09 mmol) and the solution was stirred at 70° C. for 42 h. Solvent was removed under reduced pressure and residue was purified on silica gel column chromatography (methylene chloride/ethanol 99:1 and 95:5) to yield compound 15 as a white powder (305 mg, 35%): $R_f$=0.18 (CH₂Cl₂/EtOH 95:5); mp: 256-257° C.; ¹H NMR (400 MHz, [D₆]DMSO): δ=6.65 (d, 1H, ³J=7.6 Hz), 7.31-7.37 (m, 2H), 7.46 (t, 2H, ³J=7.6 Hz), 8.01 (d, 1H, ³J=8.0 Hz), 8.33 (s, 1H), 11.63 ppm (bs, 1H); ¹³C NMR (100 MHz, [D₆]DMSO): δ=97.4, 107.9, 125.7 (2C), 128.0, 128.8 (2C), 130.0, 133.2, 143.6, 146.2, 146.3 ppm; IR (KBr): ν=3440, 3099, 1711, 1623, 1378, 1214, 1186 cm⁻¹; MS (ESI) m/z 210.0 [M+H]⁺.

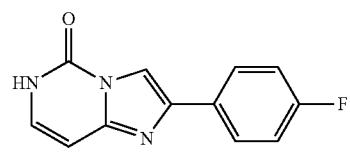 [SMILES: O=c1[nH]ccc2nc(-c3ccc(F)cc3)cn12]

2-(4-Fluorophenyl)imidazo[1,2-c]pyrimidin-5-one (16)

According to the synthesis of compound 15 starting from cytosine 1 (500 mg, 4.50 mmol) and 2-bromo-4'-fluoroacetophenone 5 (888 mg, 4.09 mmol) to yield compound 16 as a white powder (210 mg, 22%): $R_f$=0.15 (CH₂Cl₂/EtOH 95:5); mp: 310-311° C.; ¹H NMR (400 MHz, [D₆]DMSO): δ=6.65 (d, 1H, ³J=7.6 Hz), 7.27-7.34 (m, 3H), 8.04-8.08 (m, 2H), 8.35 (s, 1H), 11.66 ppm (bs, 1H); ¹³C NMR (100 MHz, [D₆]DMSO): δ=97.2, 107.6, 115.5 (2C), 127.4 (2C), 129.6, 129.9, 142.5, 146.0, 146.1, 160.8 ppm; IR (KBr): ν=3448, 3109, 1730, 1624, 1544, 1500, 1377, 1236, 1213, 836 cm⁻¹; MS (ESI) m/z 230.0 [M+H]⁺.

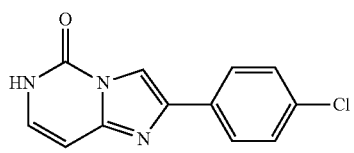 [SMILES: O=c1[nH]ccc2nc(-c3ccc(Cl)cc3)cn12]

2-(4-Chlorophenyl)imidazo[1,2-c]pyrimidin-5-one (17)

According to the synthesis of compound 15 starting from cytosine 1 (500 mg, 4.50 mmol) and 2-bromo-4'-chloroacetophenone 6 (955 mg, 4.09 mmol) to yield compound 17 as a white powder (375 mg, 37%): $R_f$=0.27 (CH$_2$Cl$_2$/EtOH 95:5); mp: 343-344° C.; $^1$H NMR (400 MHz, [D$_6$]DMSO): δ=6.65 (d, 1H, $^3$J=7.6 Hz), 7.33 (m, 1H), 7.51 (d, 2H, $^3$J=8.4 Hz), 8.04 (d, 2H, $^3$J=8.4 Hz), 8.40 (s, 1H), 11.67 ppm (bs, 1H); $^{13}$C NMR (100 MHz, [D$_6$]DMSO): δ=97.2, 108.3, 127.2 (2C), 128.7 (2C), 130.0, 132.0, 132.2, 142.2, 146.0, 146.2 ppm; IR (KBr): ν=3447, 3208, 3051, 2952, 1696, 1619, 1548, 1481, 1407, 1379, 1191, 1090, 836, 784, 746, 712, 568 cm$^{-1}$; MS (ESI) m/z 246.0-247.9 [M+H]$^+$.

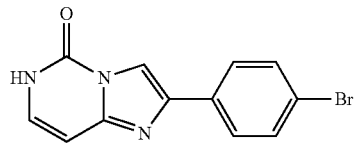 [SMILES: O=c1[nH]ccc2nc(-c3ccc(Br)cc3)cn12]

2-(4-Bromophenyl)imidazo[1,2-c]pyrimidin-5-one (18)

According to the synthesis of compound 15 starting from cytosine 1 (500 mg, 4.50 mmol) and 2,4'-dibromoacetophenone 7 (1.137 g, 4.09 mmol) to yield compound 18 as a white powder (425 mg, 36%): $R_f$=0.28 (CH$_2$Cl$_2$/EtOH 95:5); mp: 337-338° C.; NMR (400 MHz, [D$_6$]DMSO): δ=6.64 (d, 1H, $^3$J=7.2 Hz), 7.32 (m, 1H), 7.64 (d, 2H, $^3$J=8.4 Hz), 7.97 (d, 2H, $^3$J=8.4 Hz), 8.41 (s, 1H), 11.66 ppm (bs, 1H); $^{13}$C NMR (100 MHz, [D$_6$]DMSO): δ=97.2, 108.3, 120.8, 127.5 (2C), 130.0, 131.6 (2C), 132.3, 142.3, 146.0, 146.2 ppm; IR (KBr): ν=3450, 3210, 3082, 2950, 1699, 1621, 1544, 1479, 1402, 1379, 1191, 1067, 832, 796, 747, 557 cm$^{-1}$; MS (ESI) m/z 290.0-291.9 [M+H]$^+$.

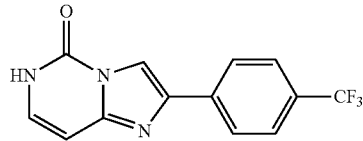

2-[(4-Trifluoromethyl)phenyl]imidazo[1,2-c]pyrimidin-5-one (19)

According to the synthesis of compound 15 starting from cytosine 1 (500 mg, 4.50 mmol) and 2-bromo-1-[4-(trifluoromethyl)phenyl]ethanone 8 (1.093 g, 4.09 mmol) to yield compound 19 as a white powder (440 mg, 39%): $R_f$=0.24 (CH$_2$Cl$_2$/EtOH 95:5); mp: 294-295° C.; $^1$H NMR (400 MHz, [D$_6$]DMSO): δ=6.67 (d, 1H, $^3$J=7.6 Hz), 7.35 (d, 1H, $^3$J=7.6 Hz), 7.80 (d, 2H, $^3$J=8.0 Hz), 8.24 (d, 2H, $^3$J=8.0 Hz), 8.54 (s, 1H), 11.67 ppm (bs, 1H); $^{13}$C NMR (100 MHz, [D$_6$]DMSO): δ=97.4, 109.8, 124.5 (q, 1C, $^1$J$_{C-F}$=272 Hz), 125.7 (d, 2C, $^3$J$_{C-F}$=4 Hz), 126.2 (2C), 128.0 (q, 1C, $^2$J$_{C-F}$=32 Hz), 130.5, 137.3, 142.0, 146.2, 146.6 ppm; IR (KBr): ν=3403, 3223, 3076, 2958, 1706, 1627, 1547, 1493, 1416, 1400, 1380, 1320, 1192, 1170, 1132, 1106, 1061, 849, 803, 764, 730, 558 cm$^{-1}$; MS (ESI) m/z 280.0 [M+H]$^+$.

Compound 8 was synthesized according a synthetic procedure reported in literature: *J. Med. Chem.* 2001, 44, 3231-3243.

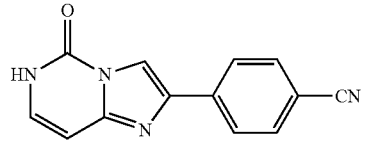 [SMILES: N#Cc1ccc(-c2cn3c(=O)[nH]ccc3n2)cc1]

2-(4-Cyanophenyl)imidazo[1,2-c]pyrimidin-5-one (20)

According to the synthesis of compound 15 starting from cytosine 1 (500 mg, 4.50 mmol) and 4-(bromoacetyl)benzonitrile 9 (917 mg, 4.09 mmol) to yield compound 20 as a white powder (300 mg, 31%): $R_f$=0.20 (CH$_2$Cl$_2$/EtOH 95:5); mp: >350° C.; $^1$H NMR (400 MHz, [D$_6$]DMSO): δ=6.67 (d, 1H, $^3$J=7.6 Hz), 7.34-7.37 (m, 1H), 7.91 (d, 2H, $^3$J=8.4 Hz), 8.20 (d, 2H, $^3$J=8.4 Hz), 8.60 (s, 1H), 11.71 ppm (d, 1H, $^3$J=4.4 Hz); $^{13}$C NMR (100 MHz, [D$_6$]DMSO): δ=98.1, 110.8, 111.2, 119.9, 127.0 (2C), 131.3, 133.6 (2C), 138.5, 142.5, 146.9, 147.4 ppm; IR (KBr): ν=3419, 3254, 3143, 2230, 1715, 1626, 1609, 1372, 1191 cm$^{-1}$; MS (ESI) m/z 237.0 [M+H]$^+$.

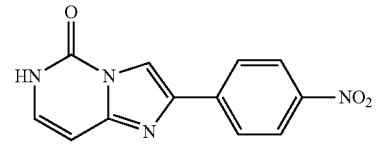 [SMILES: O=c1[nH]ccc2nc(-c3ccc([N+](=O)[O-])cc3)cn12]

2-(4-Nitrophenyl)imidazo[1,2-c]pyrimidin-5-one (21)

According to the synthesis of compound 15 starting from cytosine 1 (500 mg, 4.50 mmol) and 2-bromo-4'-nitroacetophenone 10 (998 mg, 4.09 mmol) to yield compound 21 as a white powder (210 mg, 22%): $R_f$=0.25 (CH$_2$Cl$_2$/EtOH 95:5); mp: >350° C.; NMR (400 MHz, [D$_6$]DMSO): δ=6.67 (d, 1H, $^3$J=7.2 Hz), 7.35-7.38 (m, 1H), 8.29 (s, 4H), 8.64 (s, 1H), 11.73 ppm (bs, 1H); $^{13}$C NMR (100 MHz, [D$_6$]DMSO): δ=97.4, 111.1, 124.2 (2C), 126.5 (2C), 130.8, 139.8, 141.4, 146.2, 146.7, 146.8 ppm; IR (KBr): ν=3448, 3218, 3112, 1708, 1630, 1600, 1518, 1349, 1186, 776, 738 cm$^{-1}$; MS (ESI) m/z 257.0 [M+H]$^+$.

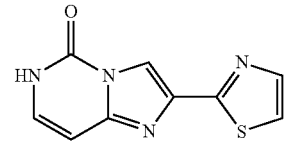 [SMILES: O=c1[nH]ccc2nc(-c3nccs3)cn12]

2-(Thiazol-2-yl)imidazo[1,2-c]pyrimidin-5-one (22)

According to the synthesis of compound 15 starting from cytosine 1 (291 mg, 2.62 mmol) and 2-bromoacetylthiazole 11 (490 mg, 2.38 mmol) to yield compound 22 as a light brown powder (85 mg, 16%): $R_f$=0.16 (CH$_2$Cl$_2$/EtOH 95:5);

mp: 327-328° C.; ¹H NMR (400 MHz, [D₆]DMSO): δ=6.69 (d, 1H, ³J=7.6 Hz), 7.38-7.41 (m, 1H), 7.81 (d, 1H, ³J=3.2 Hz), 7.96 (d, 1H, ³J=3.2 Hz), 8.16 (s, 1H), 11.83 ppm (s, 1H); ¹³C NMR (100 MHz, [D₆]DMSO): δ=97.0, 108.1, 120.4, 130.9, 138.4, 143.9, 145.9, 146.4, 161.7 ppm; IR (KBr): ν=3412, 3074, 2825, 1710, 1621, 1540, 1479, 1370, 1182, 1144, 1079, 1048, 796, 754 cm⁻¹; MS (ESI) m/z 219.0 [M+H]⁺.

Compound 11 was synthesized according a synthetic procedure reported in literature: PCT/IB2007/002000, WO 2008/004117.

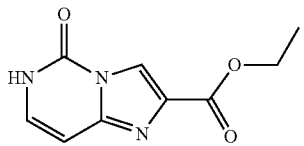

Ethyl-5-oxo-6H-imidazo[1,2-c]pyrimidine-2-carboxylate (23)

To a stirred solution of cytosine 1 (500 mg, 4.50 mmol) in MeOH (40 mL) was added ethyl 3-bromopyruvate 12 (80-85%) (0.849 mL, 5.40 mmol) and the solution was stirred at 70° C. for 15 h. Solvent was removed under reduced pressure and residue was purified on silica gel column chromatography (methylene chloride/methanol 99:1 and 95:5) to yield compound 23 as a white powder (200 mg, 21%): R_f=0.18 (CH₂Cl₂/EtOH 95:5); mp: 313-314° C.; ¹H NMR (400 MHz, [D₆]DMSO): δ=1.34 (t, 3H, ³J=7.2 Hz), 4.32 (q, 2H, ³J=7.2 Hz), 6.64 (d, 1H, ³J=7.6 Hz), 7.37-7.40 (m, 1H), 8.27 (s, 1H), 11.83 ppm (bs, 1H); ¹³C NMR (100 MHz, [D₆]DMSO): δ=14.1, 60.3, 97.5, 117.0, 131.1, 135.1, 145.9, 146.2, 161.9 ppm; IR (KBr): ν=3101, 2908, 1820, 1730, 1628, 1553, 1377, 1352, 1340, 1212, 1140 cm⁻¹; MS (ESI) m/z 208.0 [M+H]⁺.

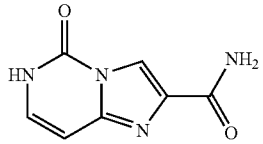 [SMILES: NC(=O)c1cn2c(=O)[nH]ccc2n1]

5-Oxo-6H-imidazo[1,2-c]pyrimidine-2-carboxamide (24)

To ethyl-5-oxo-6H-imidazo[1,2-c]pyrimidine-2-carboxylate (23) (500 mg, 2.41 mmol) in a pressure tube was added 20 mL of ammonia (20%). The tube was sealed and heated to 80° C. for 3 h. After cooling the tube was opened and the excess ammonia was removed under reduced pressure. The precipitate was filtered and washed with EtOH/Et₂O to yield compound 24 as a white powder (315 mg, 73%): R_f=0.15 (CH₂Cl₂/EtOH 90:10); mp: >350° C.; ¹H NMR (400 MHz, [D₆]DMSO): δ=6.60 (d, 1H, ³J=7.6 Hz), 7.37 (d, 1H, ³J=7.6 Hz), 7.49 (bs, 1H), 7.72 (bs, 1H), 8.09 (s, 1H), 11.06 ppm (bs, 1H); ¹³C NMR (100 MHz, [D₆]DMSO): δ=97.3, 113.4, 130.9, 139.1, 145.5, 146.1, 163.2 ppm; IR (KBr): ν=3361, 1741, 1677, 1626, 1595, 1379, 1348, 1266 cm⁻¹; MS (ESI) m/z 179.0 [M+H]⁺.

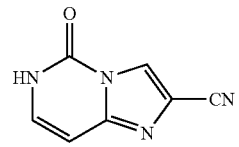 [SMILES: N#Cc1cn2c(=O)[nH]ccc2n1]

5-Oxo-6H-imidazo[1,2-c]pyrimidine-2-carbonitrile (25)

To a stirred solution of 5-oxo-6H-imidazo[1,2-c]pyrimidine-2-carboxamide (24) (540 mg, 3.03 mmol) in pyridine (21.5 mL) was added trifluoroacetic anhydride (1.27 mL, 9.09 mmol) and the solution was stirred at room temperature for 2 h. Solvent was removed under reduced pressure and residue was triturated in CH₂Cl₂/Et₂O to yield after filtration compound 25 as a white powder (330 mg, 69%): R_f=0.23 (CH₂Cl₂/EtOH 95:5); mp: 335-336° C.; ¹H NMR (400 MHz, [D₆]DMSO): δ=6.66 (d, 1H, ³J=7.6 Hz), 7.46 (m, 1H), 8.79 (s, 1H), 11.98 ppm (bs, 1H); ¹³C NMR (100 MHz, [D₆]DMSO): δ=96.9, 114.8, 115.5, 121.9, 132.3, 145.3, 146.9 ppm; IR (KBr): ν=3430, 3145, 3084, 2246, 1720, 1622, 1560, 1386, 1374, 1207, 1161 cm⁻¹; MS (ESI) m/z 160.9 [M+H]⁺.

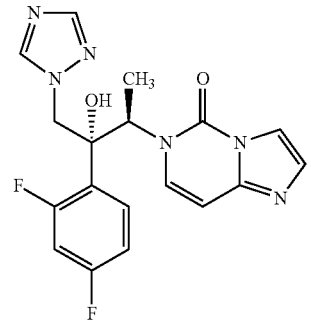 [SMILES: C[C@@H](n1ccc2nccn2c1=O)[C@](O)(Cn1cncn1)c1ccc(F)cc1F]

6-[(1R,2R)-2-(2,4-Difluorophenyl)-2-hydroxy-1-methyl-3-(1H-1,2,4-triazol-1-yl)propyl]imidazo[1,2-c]pyrimidin-5-one (27)

To a stirred solution of (2R,3S)-2-(2,4-difluorophenyl)-3-methyl-2-[(1H-1,2,4-triazol-1-yl)methyl]oxirane 26 (279 mg, 1.11 mmol) in N-methyl-2-pyrrolidone (3 mL) was added K₂CO₃ (113 mg, 0.81 mmol) and imidazo[1,2-c]pyrimidin-5-one 13 (100 mg, 0.74 mmol). The solution was stirred at 80° C. for 3 days. Mixture was diluted with water and product was extracted with ethyl acetate. Organic layers were dried over anhydrous Na₂SO₄ and concentrated in vacuo. The residue was purified on silica gel column chromatography (methylene chloride and methylene chloride/ethanol 98:2) to yield compound 27 as a white powder (235 mg, 82%): R_f=0.22 (CH₂Cl₂/EtOH 95:5); mp: 156-157° C.; [α]²⁰_D=70.0 (c=0.1 in MeOH); ¹H NMR (400 MHz, [D₆]DMSO): δ=1.17 (d, 3H, ³J=7.2 Hz), 4.39 (d, 1H, ²J=14.4 Hz), 4.87 (d, 1H, ²J=14.4 Hz), 5.72 (q, 1H, ³J=7.2 Hz), 6.28 (s, 1H), 6.81 (d, 1H, ³J=7.6 Hz), 7.02 (ddd, 1H, ³J_{H-F}=³J_{H-H}=8.4 Hz, ⁴J_{H-H}=2.0 Hz), 7.29-7.36 (m, 2H), 7.46 (s, 1H), 7.55 (d, 1H, ³J=7.6 Hz), 7.60 (s, 1H), 7.90 (s, 1H), 8.27 ppm (s, 1H); ¹³C NMR (100 MHz, [D₆]DMSO): δ=15.0, 54.1, 54.7, 77.8, 98.4, 104.4, 111.2, 113.2, 124.3, 129.9, 130.9, 132.5, 144.8, 145.0, 147.3, 150.6, 158.8, 162.3 ppm; IR (KBr): ν=3410, 3110, 1691, 1628, 1502, 1424, 1292, 1138 cm$^{-1}$; MS (ESI) m/z 387.1 [M+H]$^+$; UPLC purity 99%.

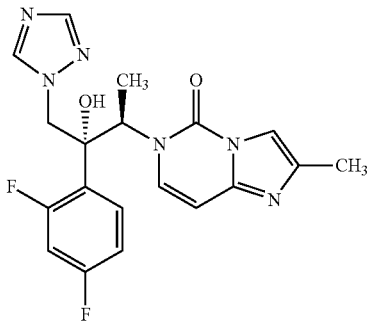 [SMILES: Cc1cn2c(=O)n([C@H](C)[C@](O)(Cn3cncn3)c3ccc(F)cc3F)ccc2n1]

6-[(1R,2R)-2-(2,4-Difluorophenyl)-2-hydroxy-1-methyl-3-(1H-1,2,4-triazol-1-yl)propyl]-2-methyl-imidazo[1,2-c]pyrimidin-5-one (28)

According to the synthesis of compound 27 starting from (2R,3S)-2-(2,4-difluorophenyl)-3-methyl-2-[(1H-1,2,4-triazol-1-yl)methyl]oxirane 26 (202 mg, 0.81 mmol) and 2-methylimidazo[1,2-c]pyrimidin-5-one 14 (80 mg, 0.54 mmol) to yield compound 28 as a white powder (160 mg, 75%): $R_f$=0.25 (CH$_2$Cl$_2$/EtOH 95:5); mp: 103-104° C.; [α]$^{20}_D$=50.0 (c=0.1 in MeOH); $^1$H NMR (400 MHz, [D$_6$]DMSO): δ=1.16 (d, 3H, $^3$J=7.2 Hz), 2.31 (s, 3H), 4.34 (d, 1H, $^2$J=14.4 Hz), 4.86 (d, 1H, $^2$J=14.4 Hz), 5.70 (q, 1H, $^3$J=7.2 Hz), 6.26 (s, 1H), 6.71 (d, 1H, $^3$J=8.0 Hz), 7.01 (ddd, 1H, $^3$J$_{H-F}$=$^3$J$_{H-H}$=8.4 Hz, $^4$J$_{H-H}$=2.0 Hz), 7.28-7.35 (m, 2H), 7.52 (d, 1H, $^3$J=8.0 Hz), 7.60 (s, 2H), 8.26 ppm (s, 1H); $^{13}$C NMR (100 MHz, [D$_6$]DMSO): δ=14.0, 15.0, 53.9, 54.7, 77.8, 97.9, 104.2, 109.3, 111.2, 124.2, 129.9, 130.7, 141.8, 144.3, 145.0, 146.9, 150.6 ppm, (CF not visible); IR (KBr): ν=3405, 1696, 1629, 1500, 1424, 1391, 1293, 1275, 1243, 1177, 1141 cm$^{-1}$; MS (ESI) m/z 401.1 [M+H]$^+$; UPLC purity 98%.

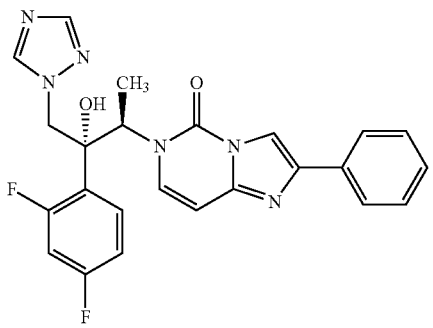 [SMILES: C[C@@H](n1ccc2nc(-c3ccccc3)cn2c1=O)[C@](O)(Cn1cncn1)c1ccc(F)cc1F]

6-[(1R,2R)-2-(2,4-Difluorophenyl)-2-hydroxy-1-methyl-3-(1H-1,2,4-triazol-1-yl)propyl]-2-phenylimidazo[1,2-c]pyrimidin-5-one (29)

According to the synthesis of compound 27 starting from (2R,3S)-2-(2,4-difluorophenyl)-3-methyl-2-[(1H-1,2,4-triazol-1-yl)methyl]oxirane 26 (178 mg, 0.71 mmol) and 2-phenylimidazo[1,2-c]pyrimidin-5-one 15 (100 mg, 0.47 mmol) to yield compound 29 as a white powder (105 mg, 48%): $R_f$=0.30 (CH$_2$Cl$_2$/EtOH 95:5); mp: 100-101° C.; [α]$^{20}_D$=60.0 (c=0.1 in MeOH); $^1$H NMR (400 MHz, [D$_6$]DMSO): δ=1.19 (d, 3H, $^3$J=7.1 Hz), 4.43 (d, 1H, $^2$J=14.4 Hz), 4.88 (d, 1H, $^2$J=14.4 Hz), 5.74 (q, 1H, $^3$J=7.4 Hz), 6.30 (s, 1H), 6.84 (d, 1H, $^3$J=8.0 Hz), 7.03 (ddd, 1H, $^3$J$_{H-F}$=$^3$J$_{H-H}$=8.4 Hz, $^4$J$_{H-H}$=2.0 Hz), 7.31-7.39 (m, 3H), 7.48 (t, 2H, $^3$J=7.6 Hz), 7.58-7.61 (m, 2H), 8.05 (d, 2H, $^3$J=7.6 Hz), 8.28 (s, 1H), 8.42 ppm (s, 1H); $^{13}$C NMR (100 MHz, [D$_6$]DMSO): δ=15.0, 54.2, 54.8, 77.8, 98.1, 104.5, 108.8, 111.2, 124.3, 125.7 (2C), 128.1, 128.9 (2C), 130.0, 131.5, 133.2, 144.0, 145.0, 145.1, 147.2, 150.6 ppm, (CF not visible); IR (KBr): ν=3448, 1701, 1629, 1420, 1274, 1247, 1141 cm$^{-1}$; MS (ESI) m/z 463.2 [M+H]$^+$; UPLC purity 99%.

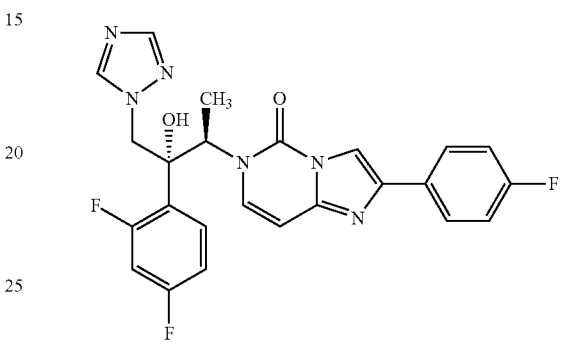

6-[(1R,2R)-2-(2,4-Difluorophenyl)-2-hydroxy-1-methyl-3-(1H-1,2,4-triazol-1-yl)propyl]-2-(4-fluorophenyl)imidazo[1,2-c]pyrimidin-5-one (30)

According to the synthesis of compound 27 starting from (2R,3S)-2-(2,4-difluorophenyl)-3-methyl-2-[(1H-1,2,4-triazol-1-yl)methyl]oxirane 26 (181 mg, 0.72 mmol) and 2-(4-fluorophenyl)imidazo[1,2-c]pyrimidin-5-one 16 (110 mg, 0.48 mmol) to yield compound 30 as a white powder (100 mg, 43%): $R_f$=0.30 (CH$_2$Cl$_2$/EtOH 95:5); mp: 114-115° C.; [α]$^{20}_D$=50.0 (c=0.1 in MeOH); $^1$H NMR (400 MHz, [D$_6$]DMSO): δ=1.19 (d, 3H, $^3$J=7.2 Hz), 4.43 (d, 1H, $^2$J=14.4 Hz), 4.88 (d, 1H, $^2$J=14.4 Hz), 5.74 (q, 1H, $^3$J=7.2 Hz), 6.29 (s, 1H), 6.83 (d, 1H, $^3$J=8.0 Hz), 7.03 (ddd, 1H, $^3$J$_{H-F}$=$^3$J$_{H-H}$=8.4 Hz, $^4$J$_{H-H}$=2.0 Hz), 7.29-7.35 (m, 4H), 7.58 (d, 1H, $^3$J=8.0 Hz), 7.61 (s, 1H), 8.08-8.11 (m, 2H), 8.27 (s, 1H), 8.43 ppm (s, 1H); $^{13}$C NMR (100 MHz, [D$_6$]DMSO): δ=14.8, 53.9, 54.5, 77.6, 97.8, 104.5, 108.5, 111.2, 115.4 (2C), 115.7 (2C), 124.3, 127.5, 127.6, 129.6, 131.4, 142.8, 144.8, 145.0, 146.9, 150.4 ppm, (CF not visible); IR (KBr): ν=3424, 1701, 1628, 1498, 1426, 1274, 1247, 1141 cm$^{-1}$; MS (ESI) m/z 481.2 [M+H]$^+$; UPLC purity 99%.

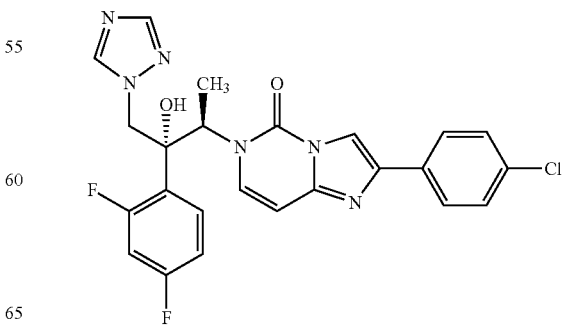

6-[(1R,2R)-2-(2,4-Difluorophenyl)-2-hydroxy-1-methyl-3-(1H-1,2,4-triazol-1-yl)propyl]-2-(4-chlorophenyl)imidazo[1,2-c]pyrimidin-5-one (31)

According to the synthesis of compound 27 starting from (2R,3S)-2-(2,4-difluorophenyl)-3-methyl-2-[(1H-1,2,4-triazol-1-yl)methyl]oxirane 26 (153 mg, 0.61 mmol) and 2-(4-chlorophenyl)imidazo[1,2-c]pyrimidin-5-one 17 (100 mg, 0.41 mmol) to yield compound 2' as a white powder (120 mg, 59%): $R_f$=0.50 ($CH_2Cl_2$/EtOH 95:5); mp: 158-159° C.; $[\alpha]^{20}_D$=50.0 (c=0.1 in MeOH); $^1$H NMR (400 MHz, [$D_6$]DMSO): δ=1.19 (d, 3H, $^3J$=6.8 Hz), 4.44 (d, 1H, $^2J$=14.4 Hz), 4.87 (d, 1H, $^2J$=14.4 Hz), 5.73 (q, 1H, $^3J$=6.8 Hz), 6.30 (s, 1H), 6.83 (d, 1H, $^3J$=8.0 Hz), 7.03 (ddd, 1H, $^3J_{H-F}$=$^3J_{H-H}$=8.4 Hz, $^4J_{H-H}$=2.0 Hz), 7.30-7.36 (m, 2H), 7.53 (d, 1H, $^3J$=8.0 Hz), 7.58-7.61 (m, 3H), 8.07 (d, 2H, $^3J$=8.4 Hz), 8.27 (s, 1H), 8.49 ppm (s, 1H); $^{13}$C NMR (100 MHz, [$D_6$]DMSO): δ=14.8, 54.0, 54.5, 77.6, 97.9, 104.2, 109.2, 111.1, 124.1, 127.2 (2C), 128.7 (2C), 129.7, 131.5, 131.9, 132.3, 142.6, 144.8, 145.1, 146.9, 150.4 ppm, (CF not visible); IR (KBr): ν=3422, 1702, 1629, 1499, 1480, 1420, 1272, 1247, 1141, 750 $cm^{-1}$; MS (ESI) m/z 497.1-499.1 [M+H]$^+$; UPLC purity 100%.

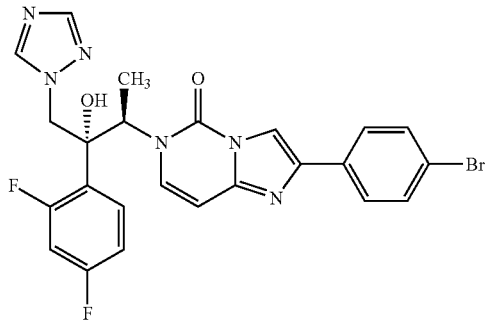 [SMILES: C[C@@H](n1ccc2nc(-c3ccc(Br)cc3)cn2c1=O)[C@](O)(Cn1cncn1)c1ccc(F)cc1F]

6-[(1R,2R)-2-(2,4-Difluorophenyl)-2-hydroxy-1-methyl-3-(1H-1,2,4-triazol-1-yl)propyl]-2-(4-bromophenyl)imidazo[1,2-c]pyrimidin-5-one (32)

According to the synthesis of compound 27 starting from (2R,3S)-2-(2,4-difluorophenyl)-3-methyl-2-[(1H-1,2,4-triazol-1-yl)methyl]oxirane 26 (156 mg, 0.62 mmol) and 2-(4-bromomethylphenyl)imidazo[1,2-c]pyrimidin-5-one 18 (120 mg, 0.41 mmol) to yield compound 32 as a white powder (152 mg, 68%): $R_f$=0.44 ($CH_2Cl_2$/EtOH 95:5); mp: 161-162° C.; $[\alpha]^{20}_D$=70.0 (c=0.1 in MeOH); NMR (400 MHz, [$D_6$]DMSO): δ=1.19 (d, 3H, $^3J$=7.2 Hz), 4.44 (d, 1H, $^2J$=14.4 Hz), 4.88 (d, 1H, $^2J$=14.4 Hz), 5.74 (q, 1H, $^3J$=7.2 Hz), 6.30 (s, 1H), 6.83 (d, 1H, $^3J$=8.0 Hz), 7.03 (ddd, 1H, $^3J_{H-F}$=$^3J_{H-H}$=8.4 Hz, $^4J_{H-H}$=2.0 Hz), 7.30-7.35 (m, 2H), 7.59 (d, 1H, $^3J$=8.0 Hz), 7.61 (s, 1H), 7.66 (d, 2H, $^3J$=8.8 Hz), 8.01 (d, 2H, $^3J$=8.8 Hz), 8.27 (s, 1H), 8.50 ppm (s, 1H); $^{13}$C NMR (100 MHz, [$D_6$]DMSO): δ=14.8, 54.0, 54.5, 77.6, 97.9, 104.2, 109.2, 111.1, 120.9, 124.1, 127.6 (2C), 129.7, 131.5, 131.6 (2C), 132.3, 142.6, 144.8, 145.1, 146.9, 150.4, 158.5, 162.0 ppm; IR (KBr): ν=3423, 3124, 1706, 1629, 1500, 1420, 1388, 1272, 1247, 1142, 747 $cm^{-1}$; MS (ESI) m/z 541.0-543.0 [M+H]$^+$; UPLC purity 100%.

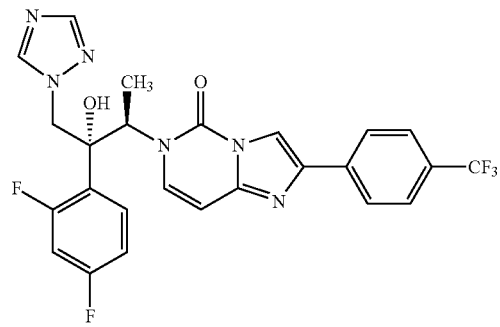 [SMILES: C[C@@H](n1ccc2nc(-c3ccc(C(F)(F)F)cc3)cn2c1=O)[C@](O)(Cn1cncn1)c1ccc(F)cc1F]

6-[(1R,2R)-2-(2,4-Difluorophenyl)-2-hydroxy-1-methyl-3-(1H-1,2,4-triazol-1-yl)propyl]-2-[(4-trifluoromethyl)phenyl]imidazo[1,2-c]pyrimidin-5-one (33)

According to the synthesis of compound 27 starting from (2R,3S)-2-(2,4-difluorophenyl)-3-methyl-2-[(1H-1,2,4-triazol-1-yl)methyl]oxirane 26 (155 mg, 0.62 mmol) and 2-[(4-trifluoromethyl)phenyl]imidazo[1,2-c]pyrimidin-5-one 19 (115 mg, 0.41 mmol) to yield compound 33 as a white powder (120 mg, 55%): $R_f$=0.41 ($CH_2Cl_2$/EtOH 95:5); mp: 196-197° C.; $[\alpha]^{20}_D$=50.0 (c=0.1 in MeOH); $^1$H NMR (400 MHz, [$D_6$]DMSO): δ=1.19 (d, 3H, $^3J$=7.2 Hz), 4.46 (d, 1H, $^2J$=14.4 Hz), 4.88 (d, 1H, $^2J$=14.4 Hz), 5.74 (q, 1H, $^3J$=7.2 Hz), 6.31 (s, 1H), 6.86 (d, 1H, $^3J$=8.0 Hz), 7.03 (ddd, 1H, $^3J_{H-F}$=$^3J_{H-H}$=8.4 Hz, $^4J_{H-H}$=2.0 Hz), 7.31-7.35 (m, 2H), 7.60-7.62 (m, 2H), 7.83 (d, 2H, $^3J$=8.0 Hz), 8.27-8.29 (m, 3H), 8.63 ppm (s, 1H); $^{13}$C NMR (100 MHz, [$D_6$]DMSO): δ=14.8, 54.0, 54.6, 77.6, 97.9, 104.2, 110.5, 111.1, 124.1, 124.3, 125.6 (2C), 126.1 (2C), 127.9, 129.7, 131.7, 137.0, 142.2, 144.8, 145.3, 147.0, 150.4, 158.5, 162.0 ppm; IR (KBr): ν=3430, 1708, 1630, 1500, 1423, 1325, 1249, 1123, 850 $cm^{-1}$; MS (ESI) m/z 531.2 [M+H]$^+$; UPLC purity 99%.

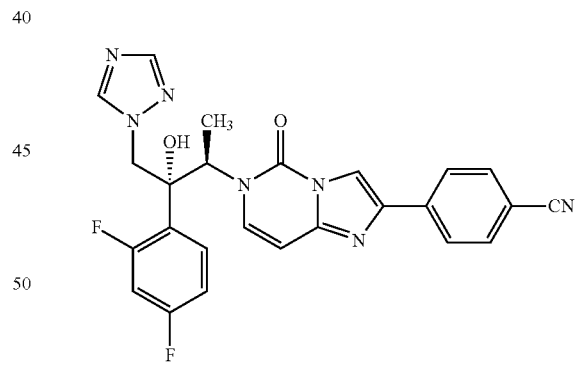

6-[(1R,2R)-2-(2,4-Difluorophenyl)-2-hydroxy-1-methyl-3-(1H-1,2,4-triazol-1-yl)propyl]-2-(4-cyanophenyl)imidazo[1,2-c]pyrimidin-5-one (34)

According to the synthesis of compound 27 starting from (2R,3S)-2-(2,4-difluorophenyl)-3-methyl-2-[(1H-1,2,4-triazol-1-yl)methyl]oxirane 26 (160 mg, 0.64 mmol) and 2-(4-cyanophenyl)imidazo[1,2-c]pyrimidin-5-one 20 (100 mg, 0.42 mmol) to yield compound 34 as a white powder (130 mg, 58%): $R_f$=0.30 ($CH_2Cl_2$/EtOH 95:5); mp: 177-178° C.; $[\alpha]^{20}_D$=90.0 (c=0.1 in MeOH); $^1$H NMR (400 MHz, [$D_6$]DMSO): δ=1.20 (d, 3H, $^3J$=7.2 Hz), 4.46 (d, 1H, $^2J$=14.4

Hz), 4.87 (d, 1H, $^2J$=14.4 Hz), 5.73 (q, 1H, $^3J$=7.2 Hz), 6.30 (s, 1H), 6.86 (d, 1H, $^3J$=8.0 Hz), 7.03 (ddd, 1H, $^3J_{H-F}$=$^3J_{H-H}$=8.4 Hz, $^4J_{H-H}$=2.0 Hz), 7.31-7.38 (m, 2H), 7.60-7.62 (m, 2H), 7.93 (d, 2H, $^3J$=8.0 Hz), 8.25 (d, 2H, $^3J$=8.0 Hz), 8.27 (s, 1H), 8.69 ppm (s, 1H); $^{13}$C NMR (100 MHz, [D$_6$]DMSO): δ=14.9, 54.2, 54.7, 77.8, 98.1, 104.4, 111.1, 111.2, 111.4, 119.1, 124.3, 126.3 (2C), 129.9, 132.1, 132.9 (2C), 137.8, 142.1, 145.0, 145.6, 147.1, 150.6 ppm, (CF not visible); IR (KBr): ν=3422, 2223, 1703, 1627, 1500, 1420, 1387, 1274, 1248 cm$^{-1}$; MS (ESI) m/z 488.1 [M+H]$^+$; UPLC purity 100%.

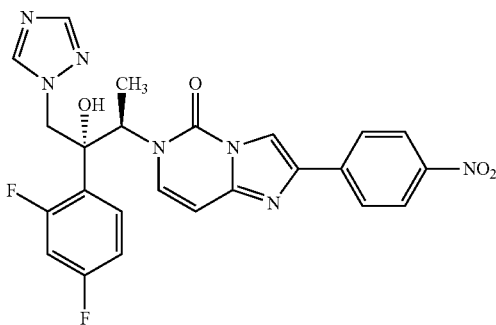 [SMILES: C[C@@H](n1ccc2nc(-c3ccc([N+](=O)[O-])cc3)cn2c1=O)[C@](O)(Cn1cncn1)c1ccc(F)cc1F]

6-[(1R,2R)-2-(2,4-Difluorophenyl)-2-hydroxy-1-methyl-3-(1H-1,2,4-triazol-1-yl)propyl]-2-(4-nitrophenyl)imidazo[1,2-c]pyrimidin-5-one (35)

According to the synthesis of compound 27 starting from (2R,3S)-2-(2,4-difluorophenyl)-3-methyl-2-[(1H-1,2,4-triazol-1-yl)methyl]oxirane 26 (147 mg, 0.59 mmol) and 2-(4-nitrophenyl)imidazo[1,2-c]pyrimidin-5-one 21 (100 mg, 0.39 mmol) to yield compound 35 as a yellow powder (100 mg, 50%): R$_f$=0.35 (CH$_2$Cl$_2$/EtOH 95:5); mp: 209-210° C.; [α]$^{20}_D$=70.0 (c=0.1 in MeOH); $^1$H NMR (400 MHz, [D$_6$] DMSO): δ=1.20 (d, 3H, $^3J$=7.2 Hz), 4.47 (d, 1H, $^2J$=14.4 Hz), 4.87 (d, 1H, $^2J$=14.4 Hz), 5.73 (q, 1H, $^3J$=7.2 Hz), 6.31 (s, 1H), 6.86 (d, 1H, $^3J$=8.0 Hz), 7.03 (ddd, 1H, $^3J_{H-F}$=$^3J_{H-H}$=8.4 Hz, $^2J_{H-H}$=2.0 Hz), 7.31-7.37 (m, 2H), 7.61-7.63 (m, 2H), 8.27-8.34 (m, 5H), 8.75 ppm (s, 1H); $^{13}$C NMR (100 MHz, [D$_6$]DMSO): δ=14.7, 54.1, 54.5, 77.6, 97.9, 104.3, 111.1, 111.8, 124.0, 124.1 (2C), 126.3 (2C), 129.7, 132.0, 139.6, 141.6, 144.8, 145.5, 146.6, 146.9, 150.4 ppm, (CF not visible); IR (KBr): ν=3431, 1709, 1629, 1603, 1506, 1424, 1334, 1247 cm$^{-1}$; MS (ESI) m/z 508.2 [M+H]$^+$; UPLC purity 100%.

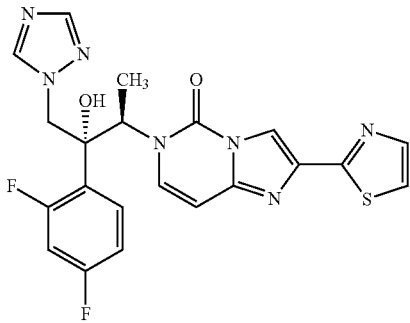 [SMILES: C[C@@H](n1ccc2nc(-c3nccs3)cn2c1=O)[C@](O)(Cn1cncn1)c1ccc(F)cc1F]

6-[(1R,2R)-2-(2,4-Difluorophenyl)-2-hydroxy-1-methyl-3-(1H-1,2,4-triazol-1-yl)propyl]-2-(thiazol-2-yl)imidazo[1,2-c]pyrimidin-5-one (36)

According to the synthesis of compound 27 starting from (2R,3S)-2-(2,4-difluorophenyl)-3-methyl-2-[(1H-1,2,4-triazol-1-yl)methyl]oxirane 26 (112 mg, 0.45 mmol) and 2-(thiazol-2-yl)imidazo[1,2-c]pyrimidin-5-one 22 (65 mg, 0.30 mmol) to yield compound 36 as a yellow powder (75 mg, 54%): R$_f$=0.25 (CH$_2$Cl$_2$/EtOH 95:5); mp: 175-176° C.; [α]$^{20}_D$=70.0 (c=0.1 in MeOH); $^1$H NMR (400 MHz, [D$_6$] DMSO): δ=1.19 (d, 3H, $^3J$=7.2 Hz), 4.48 (d, 1H, $^2J$=14.4 Hz), 4.86 (d, 1H, $^2J$=14.4 Hz), 5.72 (q, 1H, $^3J$=7.2 Hz), 6.32 (s, 1H), 6.86 (d, 1H, $^3J$=8.0 Hz), 7.03 (ddd, 1H, $^3J_{H-F}$=$^3J_{H-H}$=8.4 Hz, $^4J_{H-H}$=2.0 Hz), 7.31-7.37 (m, 2H), 7.61 (s, 1H), 7.63 (d, 1H, $^3J$=8.0 Hz), 7.83 (d, 1H, $^3J$=3.2 Hz), 7.98 (d, 1H, $^3J$=3.2 Hz), 8.26 (s, 1H), 8.27 ppm (s, 1H); $^{13}$C NMR (100 MHz, [D$_6$]DMSO): δ=14.7, 54.2, 54.5, 77.6, 97.7, 104.3, 109.1, 111.1, 120.5, 124.0, 129.7, 132.3, 138.7, 143.9, 144.8, 145.3, 146.9, 150.4, 161.6 ppm, (CF not visible); IR (KBr): ν=3403, 3100, 2925, 1706, 1626, 1498, 1420, 1273, 1246, 1178, 1143, 1050, 966, 851, 763 cm$^{-1}$; MS (ESI) m/z 470.1 [M+H]$^+$; UPLC purity 100%.

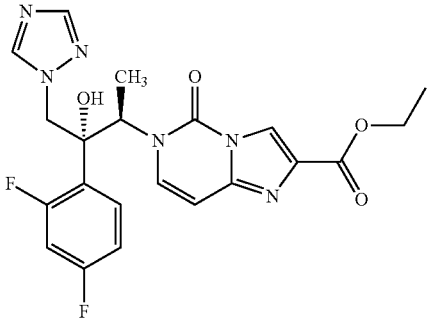 [SMILES: CCOC(=O)c1cn2c(=O)n([C@H](C)[C@](O)(Cn3cncn3)c3ccc(F)cc3F)ccc2n1]

Ethyl-6-[(1R,2R)-2-(2,4-difluorophenyl)-2-hydroxy-1-methyl-3-(1H-1,2,4-triazol-1-yl)propyl]-5-oxo-imidazo[1,2-c]pyrimidine-2-carboxylate (37)

According to the synthesis of compound 27 starting from (2R,3S)-2-(2,4-difluorophenyl)-3-methyl-2-[(1H-1,2,4-triazol-1-yl)methyl]oxirane 26 (182 mg, 0.72 mmol) and ethyl-5-oxo-6H-imidazo[1,2-c]pyrimidine-2-carboxylate 23 (100 mg, 0.48 mmol) to yield compound 37 as a white powder (80 mg, 36%): R$_f$=0.28 (CH$_2$Cl$_2$/EtOH 95:5); mp: 148-149° C.; [α]$^{20}_D$=70.0 (c=0.1 in MeOH); NMR (400 MHz, [D$_6$] DMSO): δ=1.18 (d, 3H, $^3J$=7.2 Hz), 1.36 (t, 3H, $^3J$=6.8 Hz), 4.35 (q, 2H, $^3J$=6.8 Hz), 4.48 (d, 1H, $^2J$=14.4 Hz), 4.83 (d, 1H, $^2J$=14.4 Hz), 5.39 (q, 1H, $^3J$=7.2 Hz), 6.32 (s, 1H), 6.81 (d, 1H, $^3J$=8.0 Hz), 7.04 (ddd, 1H, $^3J_{H-F}$=$^3J_{H-H}$=8.4 Hz, $^4J_{H-H}$=2.0 Hz), 7.30-7.37 (m, 2H), 7.60 (s, 1H), 7.62 (d, 1H, $^3J_{H-H}$=8.0 Hz), 8.26 (s, 1H), 8.66 ppm (s, 1H); $^{13}$C NMR (100 MHz, [D$_6$]DMSO): δ=14.3, 14.7, 54.2, 54.5, 60.4, 77.5, 98.2, 104.2, 111.1, 117.9, 124.2, 129.6, 132.6, 135.4, 144.8, 145.1, 146.9, 150.4, 158.7, 161.9, 162.1 ppm; IR (KBr): ν=3420, 2926, 1709, 1631, 1500, 1422, 1374, 1273, 1249, 1201, 1139 cm$^{-1}$; MS (ESI) m/z 459.1 [M+H]$^+$; UPLC purity 98%.

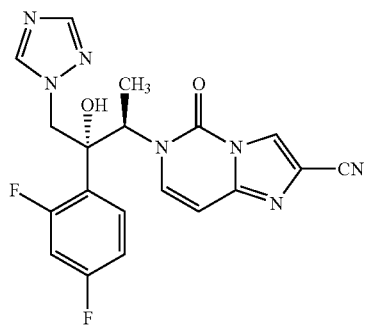 [SMILES: C[C@@H](n1ccc2nc(C#N)cn2c1=O)[C@](O)(Cn1cncn1)c1ccc(F)cc1F]

6-[(1R,2R)-2-(2,4-Difluorophenyl)-2-hydroxy-1-methyl-3-(1H-1,2,4-triazol-1-yl)propyl]-5-oxo-imidazo[1,2-c]pyrimidine-2-carbonitrile (38)

According to the synthesis of compound 27 starting from (2R,3S)-2-(2,4-difluorophenyl)-3-methyl-2-[(1H-1,2,4-triazol-1-yl)methyl]oxirane 26 (247 mg, 0.98 mmol) and 5-oxo-6H-imidazo[1,2-c]pyrimidine-2-carbonitrile 25 (105 mg, 0.66 mmol) to yield compound 38 as a white powder (75 mg, 28%): $R_f$=0.33 (CH$_2$Cl$_2$/EtOH 95:5); mp: 132-133° C.; $[\alpha]^{20}_D$=80.0 (c=0.1 in MeOH); $^1$H NMR (400 MHz, [D$_6$] DMSO): δ=1.17 (d, 3H, $^3J$=7.2 Hz), 4.51 (d, 1H, $^2J$=14.4 Hz), 4.79 (d, 1H, $^2J$=14.4 Hz), 5.67 (q, 1H, $^3J$=7.2 Hz), 6.33 (s, 1H), 6.84 (d, 1H, $^3J$=8.0 Hz), 7.04 (ddd, 1H, $^3J_{H-F}$=$^3J_{H-H}$=8.4 Hz, $^4J_{H-H}$=2.0 Hz), 7.31-7.37 (m, 2H), 7.60 (s, 1H), 7.67 (d, 1H, $^3J$=8.0 Hz), 8.25 (s, 1H), 8.90 ppm (s, 1H); $^{13}$C NMR (100 MHz, [D$_6$]DMSO): δ=14.6, 54.3, 54.4, 77.5, 97.5, 104.3, 111.1, 114.8, 115.8, 122.8, 124.1, 129.7, 133.7, 144.8, 145.8, 146.4, 150.4, 158.4, 162.2 ppm; IR (KBr): ν=3412, 3129, 2237, 1718, 1631, 1503, 1424, 1276, 1246, 1172, 1142, 968 cm$^{-1}$; MS (ESI) m/z 412.1 [M+H]$^+$; UPLC purity 100%.

Scheme 3.

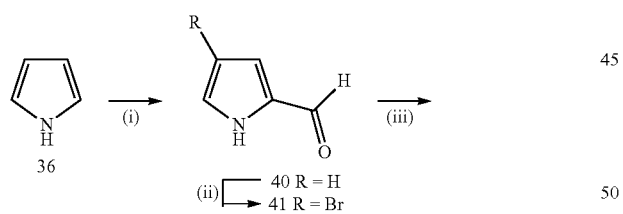

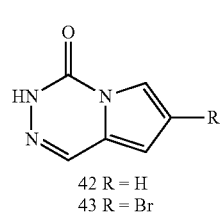

42 R = H
43 R = Br

Reagents and conditions: (i) POCl$_3$, DMF, 1,2-dichloroethane, AcONa, 0° C. to reflux, 20'; (ii) NBS, CH$_3$CN, 0° C., 15'; (iii) a) H$_2$NNHCOOEt, DMF, 90° C., 24 h; b) NaH, DMF, 90° C., 24 h.

Scheme 4.

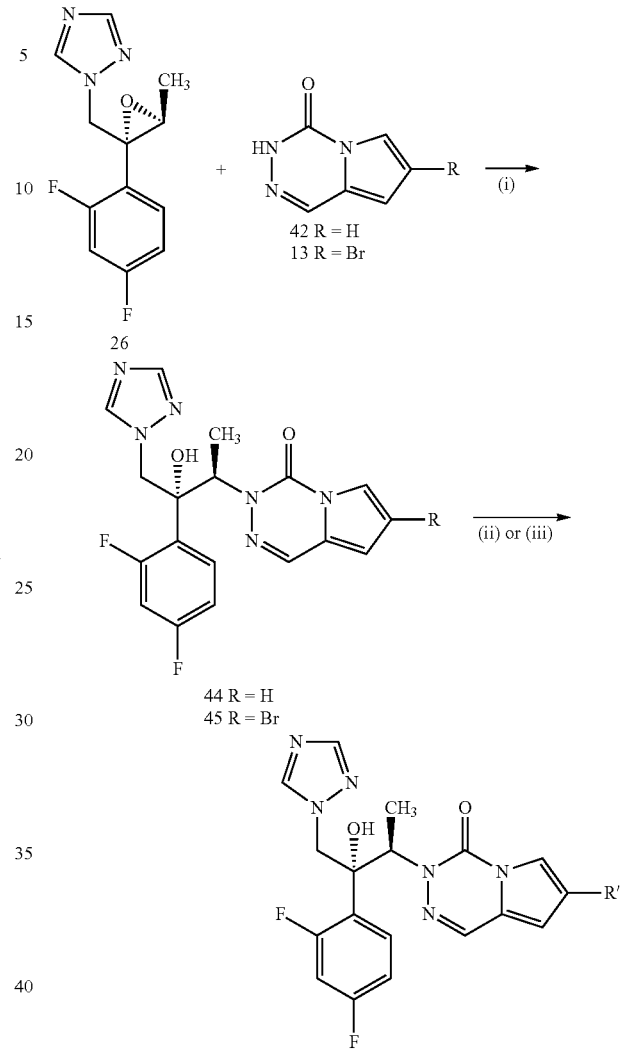

46 R' = CN
47 R' = Ph
48 R' = 4-Cl—Ph
49 R' = 4-CN—Ph
50 R' = 4-NO$_2$—Ph
51 R' = 4-OCH$_3$—Ph

Reagents and conditions: (i) K$_2$CO$_3$, NMP, 80° C., 3 days; (ii) starting from cpd 45: ZN(CN)$_2$, Pd(PPh$_3$)$_4$, DMF, 120° C. (mW), 10'; (iii) starting from cpd 45:Ar—B(OH)$_2$, Pd(PPh$_3$)$_4$, ACN, Na$_2$CO$_3$, 120° C. (mW), 10'.

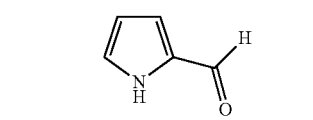

1H-Pyrrole-2-carboxaldehyde (40)

To 6.35 mL of DMF at 0° C. (82.0 mmol) under argon was added dropwise 7.5 mL of phosphorus oxychloride (82.0 mmol). The cooling bath was removed and stirring was continued for 15 mn. The solution was diluted with 1,2-dichloroethane (18 mL) and cooled again to 0° C. A solution of 1H-pyrrole (5.17 mL, 74.5 mmol) in 1,2-dichloroethane (18 mL) was added dropwise. The mixture was heated to reflux for 15 min and cooled to 0° C. Then a solution of sodium acetate (33.55 g, 409.8 mmol) in water (90 mL) was added with vigorous stirring. The mixture was heated at reflux for 20 min and allowed to cool to room temperature. The mixture was diluted with sat NaHCO$_3$ and product was extracted with methylene chloride. Organic layers were dried over anhydrous Na$_2$SO$_4$ and concentrated in vacuo. The residue was purified on silica gel column chromatography (methylene chloride) to yield compound 40 as orange crystals (6.37 g, 90%): R$_f$=0.36 (CH$_2$Cl$_2$/EtOH 99:1); mp: 45-46° C.; NMR (400 MHz, [D$_6$]DMSO): δ=6.31 (m, 1H), 7.03 (m, 1H), 7.25 (m, 1H), 9.51 (s, 1H), 12.14 ppm (bs, 1H); IR (KBr): ν=3153, 2978, 2865, 1638, 1444, 1405, 1356, 1315, 1140, 1097, 1049, 863, 753, 605, 518 cm$^{-1}$; MS (ESI) m/z 95.8 [M+H]$^+$.

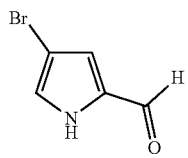

4-Bromo-1H-pyrrole-2-carboxaldehyde (41)

To a stirred solution of 1H-pyrrole-2-carboxaldehyde 40 (1 g, 10.52 mmol) in CH$_3$CN (10 mL) at 0° C. was added N-bromosuccinimide (1.872 g, 10.52 mmol) and the solution was stirred at 0° C. for 15 minutes. Water was added and the resulting mixture was extracted with Et$_2$O. Organic layers were dried over anhydrous Na$_2$SO$_4$ and concentrated in vacuo. Crystallization of the crude mixture using cyclohexane/ethanol afforded compound 41 as white crystals (1.125 g, 61%): R$_f$=0.22 (CH$_2$Cl$_2$); mp: 121-122° C.; $^1$H NMR (400 MHz, [D$_6$]DMSO): δ=7.12 (m, 1H), 7.41 (m, 1H), 9.48 (s, 1H), 12.51 ppm (bs, 1H); $^{13}$C NMR (100 MHz, [D$_6$]DMSO): δ=97.0, 120.8, 126.5, 132.9, 179.1 ppm; IR (KBr): ν=3238, 3108, 2926, 2860, 1655, 1380, 1357, 1147, 1104, 920, 827, 771, 744, 598 cm$^{-1}$, MS (ESI) m/z 173.9-175.9 [M+H]$^+$.

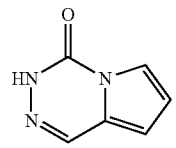

3H-Pyrrolo[1,2-d][1,2,4]triazin-4-one (42)

To a stirred solution of ethylcarbazate (241 mg, 2.31 mmol) in DMF (5 mL) was added 1H-pyrrole-2-carboxaldehyde (200 mg, 2.10 mmol) and the solution was stirred at 90° C. for 24 h. The solution was cooled to 0° C., sodium hydride (60% dispersion in mineral oil) (42 mg, 1.05 mmol) was added and the reaction mixture was stirred at 90° C. for 24 h. Water was added and the resulting mixture was extracted with ethyl acetate. Organic layers were washed with brine, dried over anhydrous Na$_2$SO$_4$ and concentrated in vacuo. The residue was purified on silica gel column chromatography (petroleum ether/diethyl ether 7:3) to yield compound 42 as a white powder (172 mg, 61%): R$_f$=0.31 (Petroleum ether/Et$_2$O 1:1); mp: 160-161° C.; NMR (400 MHz, [D$_6$]DMSO): δ=6.86 (m, 2H), 7.79 (m, 1H), 8.28 (s, 1H), 12.29 ppm (bs, 1H); $^{13}$C NMR (100 MHz, [D$_6$]DMSO): δ=109.1, 115.4, 116.2, 125.6, 132.4, 144.7 ppm; IR (KBr): ν=3238, 3200, 3147, 3100, 2996, 2935, 1718, 1602, 1438, 1421, 1352, 1313, 1260, 1215, 1163, 1081, 875, 762, 732, 626 cm$^{-1}$; MS (ESI) m/z 135.8 [M+H]$^+$.

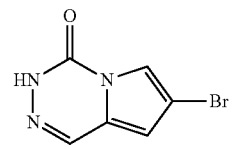

7-Bromo-3H-pyrrolo[1,2-d][1,2,4]triazin-4-one (43)

According to the synthesis of 3H-pyrrolo[1,2-d][1,2,4]triazin-4-one 42 starting from 4-bromo-1H-pyrrole-2-carboxaldehyde 41 (1 g, 5.75 mmol) and ethylcarbazate (658 mg, 6.32 mmol) to yield compound 43 as a white powder (600 mg, 49%): R$_f$=0.24 (CH$_2$Cl$_2$/EtOH 99:1); mp: 187-188° C.; NMR (400 MHz, [D$_6$]DMSO): δ=6.99 (s, 1H), 7.96 (d, 1H, $^4$J=0.8 Hz), 8.24 (s, 1H), 12.48 ppm (bs, 1H); $^{13}$C NMR (100 MHz, [D$_6$]DMSO): δ=104.4, 110.6, 115.8, 126.3, 131.3, 143.3 ppm; IR (KBr): ν=3203, 3151, 3102, 1717, 1533, 1474, 1409, 1383, 1327, 1302, 1147, 891, 825, 727, 628 cm$^{-1}$; MS (ESI) m/z 214.0-216.0 [M+H]$^+$.

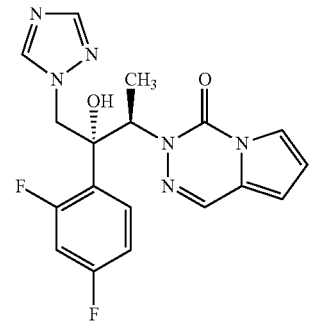

3-[(1R,2R)-2-(2,4-Difluorophenyl)-2-hydroxy-1-methyl-3-(1,2,4-triazol-1-yl)propyl]-3H-pyrrolo[1,2-d][1,2,4]triazin-4-one (44)

To a stirred solution of (2R,3S)-2-(2,4-difluorophenyl)-3-methyl-2-[(1H-1,2,4-triazol-1-yl)methyl]oxirane 26 (279 mg, 1.11 mmol) in N-methyl-2-pyrrolidone (3 mL) was added K$_2$CO$_3$ (113 mg, 0.81 mmol) and 3H-pyrrolo[1,2-d][1,2,4]triazin-4-one 42 (100 mg, 0.74 mmol). The solution was stirred at 80° C. for 3 days. Mixture was diluted with water and product was extracted with ethyl acetate. Organic layers were dried over anhydrous Na$_2$SO$_4$ and concentrated in vacuo. The residue was purified on silica gel column chromatography (Et$_2$O) to yield compound 44 as a white powder (140 mg, 49%): R$_f$=0.10 (Et$_2$O); mp: 131-132° C.; [α]$^{20}$$_D$=30.0 (c=0.1 in MeOH); $^1$H NMR (400 MHz, [D$_6$]DMSO): δ=1.22 (d, 3H, $^3$J=6.8 Hz), 4.48 (d, 1H, $^2$J=14.4 Hz), 4.91 (d, 1H, $^2$J=14.4 Hz), 5.64-5.69 (m, 2H), 6.91-6.99 (m, 3H), 7.25 (ddd, 1H, $^3$J$_{H-F}$=$^3$J'$_{H-F}$=9.2 Hz, $^4$J$_{H-F}$=2.0 Hz), 7.35 (ddd, 1H, $^3$J$_{H-H}$=8.4 Hz, $^4$J$_{H-F}$=$^4$J'$_{H-F}$=6.8 Hz), 7.59 (s, 1H), 7.89 (s, 1H), 8.29 (s, 1H), 8.48 (s, 1H); $^{13}$C NMR (100 MHz, [D$_6$]DMSO): δ=14.1, 54.7, 55.5, 77.4, 103.9, 109.6, 110.9, 116.0, 117.5, 124.0, 125.0, 130.0, 132.7, 144.7, 145.0, 150.2, 158.7, 161.9 ppm; IR (KBr): ν=3398, 3126, 1706, 1676, 1617, 1598, 1499, 1448, 1424, 1344, 1272, 1164, 1139, 963, 732, 682 cm$^{-1}$; MS (ESI) m/z 387.1 [M+H]$^+$; UPLC purity 99%.

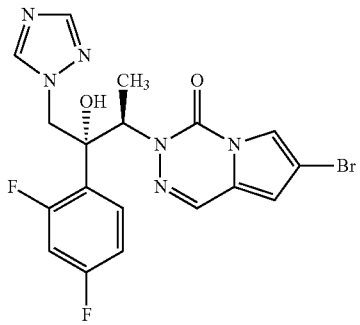 [SMILES: C[C@@H](n1ncc2cc(Br)cn2c1=O)[C@](O)(Cn1cncn1)c1ccc(F)cc1F]

7-Bromo-3-[(1R,2R)-2-(2,4-difluorophenyl)-2-hydroxy-1-methyl-3-(1,2,4-triazol-1-yl)propyl]-3H-pyrrolo[1,2-d][1,2,4]triazin-4-one (45)

According to the synthesis of 3-[(1R,2R)-2-(2,4-difluorophenyl)-2-hydroxy-1-methyl-3-(1H-1,2,4-triazol-1-yl)propyl]pyrrolo[1,2-d][1,2,4]triazin-4-one 44 starting from (2R,3S)-2-(2,4-difluorophenyl)-3-methyl-2-[(1H-1,2,4-triazol-1-yl)methyl]oxirane 26 (880 mg, 3.51 mmol) and 7-bromo-3H-pyrrolo[1,2-d][1,2,4]triazin-4-one 43 (500 mg, 2.34 mmol). The residue was purified on silica gel column chromatography (diethyl ether/ethyl acetate 50:50) followed by C18 reverse-phase column chromatography (acetonitrile/water 40:60) to yield compound 45 as a light brown powder (480 mg, 44%): R$_f$=0.27 (CH$_2$Cl$_2$/EtOH 98:2); mp: 142-143° C.; [α]$^{20}$$_D$=20.0 (c=0.1 in MeOH); NMR (400 MHz, [D$_6$]DMSO): δ=1.22 (d, 3H, $^3$J=7.2 Hz), 4.50 (d, 1H, $^2$J=14.4 Hz), 4.89 (d, 1H, $^2$J=14.4 Hz), 5.60-5.62 (m, 2H), 6.96 (ddd, 1H, $^3$J$_{H-F}$=$^3$J$_{H-H}$=8.4 Hz, $^4$J$_{H-H}$=2.6 Hz), 7.06 (d, 1H, $^4$J=1.2 Hz), 7.24 (ddd, 1H, $^3$J$_{H-F}$=$^3$J'$_{H-F}$=9.2 Hz, $^4$J$_{H-H}$=2.6 Hz), 7.34 (m, 1H), 7.60 (s, 1H), 8.05 (d, 1H, $^4$J=1.2 Hz), 8.27 (s, 1H), 8.43 (s, 1H); $^{13}$C NMR (100 MHz, [D$_6$]DMSO): δ=14.1, 54.7, 55.9, 77.4, 103.9, 104.8, 111.0 (2C), 117.0, 124.0, 125.7, 130.0, 131.5, 143.7, 144.7, 150.2, 158.7, 161.9 ppm; IR (KBr): ν=3376, 3159, 1706, 1617, 1499, 1458, 1401, 1329, 1294, 1272, 1173, 1133, 1043, 961, 852, 727, 670 cm$^{-1}$; MS (ESI) m/z 465.0-466.9 [M+H]$^+$; UPLC purity 100%.

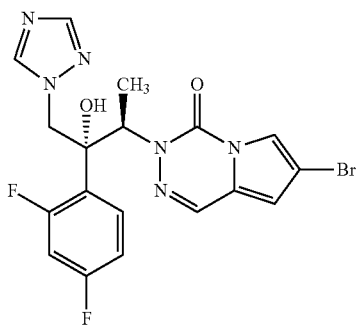 [SMILES: C[C@@H](n1ncc2cc(Br)cn2c1=O)[C@](O)(Cn1cncn1)c1ccc(F)cc1F]

3-[(1R,2R)-2-(2,4-Difluorophenyl)-2-hydroxy-1-methyl-3-(1,2,4-triazol-1-yl)propyl]-4-oxo-3,4-dihydro-pyrrolo[1,2-d][1,2,4]triazine-7-carbonitrile (46)

To a 10 mL vial were added under argon 7-bromo-3-[(1R,2R)-2-(2,4-difluorophenyl)-2-hydroxy-1-methyl-3-(1,2,4-triazol-1-yl)propyl]-3H-pyrrolo[1,2-d][1,2,4]triazin-4-one 45 (200 mg, 0.43 mmol), zinc cyanide (50 mg, 0.43 mmol), Pd(PPh$_3$)$_4$ (25 mg, 0.02 mmol) and DMF (2 mL). The resulting mixture was heated at 120° C. under microwave irradiation for 10 min. The reaction mixture was cooled to room temperature and diluted with water. Product was extracted with ethyl acetate, organic layers were dried over anhydrous Na$_2$SO$_4$ and concentrated in vacuo. The residue was purified on silica gel column chromatography (diethyl ether/ethyl acetate 80:20), then triturated in diisopropyl ether to yield after filtration compound 46 as a white powder (92 mg, 52%): R$_f$=0.30 (CH$_2$Cl$_2$/EtOH 98:2); mp: 218-219° C.; [α]$^{20}$$_D$=10.0 (c=0.1 in MeOH); NMR (400 MHz, [D$_6$]DMSO): δ=1.22 (d, 3H, $^3$J=6.8 Hz), 4.56 (d, 1H, $^2$J=14.4 Hz), 4.88 (d, 1H, $^2$J=14.4 Hz), 5.59 (d, 1H, $^3$J=6.8 Hz), 5.69 (s, 1H), 6.97 (ddd, 1H, $^3$J$_{H-F}$=$^3$J$_{H-H}$=8.8 Hz, $^4$J$_{H-H}$=2.2 Hz), 7.26 (ddd, 1H, $^3$J$_{H-F}$=$^3$J'$_{H-F}$=9.2 Hz, $^4$J$_{H-H}$=2.2 Hz), 7.31-7.37 (m, 2H), 7.60 (s, 1H), 8.27 (s, 1H), 8.52 (s, 1H), 8.71 (s, 1H); $^{13}$C NMR (100 MHz, [D$_6$]DMSO): δ=13.8, 54.6, 56.2, 77.4, 99.1, 104.0, 111.0 (2C), 114.9, 124.0, 124.4, 125.7, 130.0, 132.3, 144.0, 144.7, 150.2, 158.7, 161.9 ppm; IR (KBr): ν=3335, 2233, 1718, 1612, 1508, 1431, 1407, 1310, 1167, 1136, 1042, 959, 890, 829, 730, 673 cm$^{-1}$; MS (ESI) m/z 412.1 [M+H]$^+$; UPLC purity 94%.

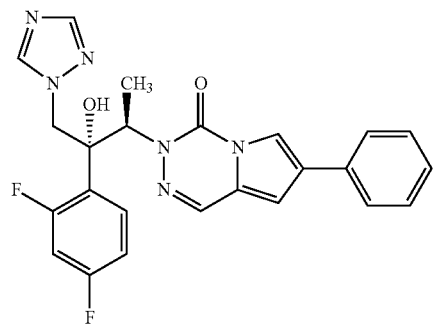

3-[(1R,2R)-2-(2,4-Difluorophenyl)-2-hydroxy-1-methyl-3-(1,2,4-triazol-1-yl)propyl]-7-phenyl-3H-pyrrolo[1,2-d][1,2,4]triazin-4-one (47)

To a 10 mL vial were added under argon 7-bromo-3-[(1R,2R)-2-(2,4-difluorophenyl)-2-hydroxy-1-methyl-3-(1,2,4-triazol-1-yl)propyl]-3H-pyrrolo[1,2-d][1,2,4]triazin-4-one 45 (200 mg, 0.43 mmol), benzeneboronic acid (61 mg, 0.43 mmol), Pd(PPh$_3$)$_4$ (25 mg, 0.02 mmol), 2M Na$_2$CO$_3$ aqueous solution (2 mL) and acetonitrile (2 mL). The resulting mixture was heated at 120° C. under microwave irradiation for 10 min. The reaction mixture was cooled to room temperature and diluted with water. Product was extracted with methylene chloride, organic layers were dried over anhydrous Na$_2$SO$_4$ and concentrated in vacuo. The residue was purified on silica gel column chromatography (CH$_2$Cl$_2$ and CH$_2$Cl$_2$/EtOH 99:1) to yield compound 47 as a green powder (119 mg, 60%): R$_f$=0.29 (CH$_2$Cl$_2$/EtOH 98:2); mp: 146-147° C.; [α]$^{20}$$_D$=80.0 (c=0.1 in MeOH); $^1$H NMR (400

MHz, [D₆]DMSO): δ=1.24 (d, 3H, $^3J$=6.8 Hz), 4.53 (d, 1H, $^2J$=14.4 Hz), 4.94 (d, 1H, $^2J$=14.4 Hz), 5.65-5.71 (m, 2H), 6.97 (ddd, 1H, $^3J_{H-F}$=$^3J_{H-H}$=8.4 Hz, $^4J_{H-H}$=2.4 Hz), 7.26 (ddd, 1H, $^3J_{H-F}$=$^3J'_{H-F}$=9.2 Hz, $^4J_{H-H}$=2.4 Hz), 7.33-7.39 (m, 3H), 7.48 (d, 2H, $^3J_{H-H}$=7.3 Hz), 7.60 (s, 1H), 7.89 (d, 2H, $^3J_{H-H}$=7.3 Hz), 8.30 (s, 1H), 8.37 (s, 1H), 8.49 (s, 1H); $^{13}$C NMR (100 MHz, [D₆]DMSO): δ=14.1, 54.8, 55.5, 77.4, 104.0, 106.7, 111.0, 113.9, 124.1, 125.9, 126.0 (2C), 127.6, 129.0 (2C), 130.1, 130.7, 132.5, 132.7, 144.7, 144.8, 157.5, 158.7, 161.9 ppm; IR (KBr): ν=3403, 1696, 1617, 1500, 1458, 1408, 1272, 1210, 1133, 1045, 964, 851, 758, 728, 677, 511 cm$^{-1}$; MS (ESI) m/z 463.1 [M+H]⁺; UPLC purity 100%.

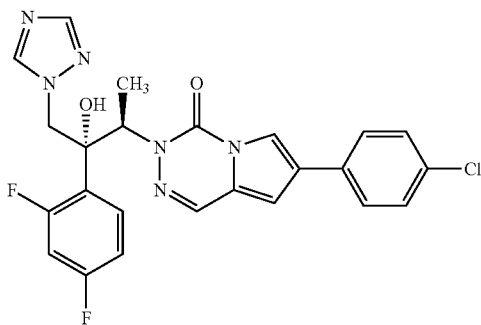 [SMILES: C[C@@H](n1ncc2cc(-c3ccc(Cl)cc3)cn2c1=O)[C@](O)(Cn1cncn1)c1ccc(F)cc1F]

7-(4-Chlorophenyl)-3-[(1R,2R)-2-(2,4-difluorophenyl)-2-hydroxy-1-methyl-3-(1,2,4-triazol-1-yl)propyl]-3H-pyrrolo[1,2-d][1,2,4]triazin-4-one (48)

According to the synthesis of 3-[(1R,2R)-2-(2,4-difluorophenyl)-2-hydroxy-1-methyl-3-(1,2,4-triazol-1-yl)propyl]-7-phenyl-3H-pyrrolo[1,2-d][1,2,4]triazin-4-one 47 starting from 7-bromo-3-[(1R,2R)-2-(2,4-difluorophenyl)-2-hydroxy-1-methyl-3-(1,2,4-triazol-1-yl)propyl]-3H-pyrrolo[1,2-d][1,2,4]triazin-4-one 45 (200 mg, 0.43 mmol) and 4-chlorobenzeneboronic acid (61 mg, 0.43 mmol) to yield compound 48 as a light yellow powder (98 mg, 46%): $R_f$=0.25 (CH₂Cl₂/EtOH 98:2); mp: 204-205° C.; [α]$^{20}_D$=30.0 (c=0.1 in MeOH); $^1$H NMR (400 MHz, [D₆]DMSO): δ=1.24 (d, 3H, $^3J$=6.8 Hz), 4.53 (d, 1H, $^2J$=14.4 Hz), 4.93 (d, 1H, $^2J$=14.4 Hz), 5.65-5.66 (m, 2H), 6.98 (ddd, 1H, $^3J_{H-F}$=$^3J_{H-H}$=8.8 Hz, $^4J_{H-H}$=2.2 Hz), 7.26 (ddd, 1H, $^3J_{H-F}$=$^3J_{H-F}$=9.2 Hz, $^4J_{H-H}$=2.2 Hz), 7.33-7.38 (m, 2H), 7.53 (d, 2H, $^3J_{H-H}$=8.4 Hz), 7.60 (s, 1H), 7.93 (d, 2H, $^3J_{H-H}$=8.4 Hz), 8.29 (s, 1H), 8.42 (s, 1H), 8.48 (s, 1H); $^{13}$C NMR (100 MHz, [D₆]DMSO): δ=14.1, 54.7, 55.8, 77.4, 103.9, 106.7, 111.0, 114.2, 124.1, 125.9, 126.6, 127.8 (2C), 128.9 (2C), 129.4, 130.1, 131.7, 132.1, 132.5, 144.7, 150.2, 158.7, 161.9 ppm; IR (KBr): ν=3386, 1707, 1599, 1500, 1386, 1293, 1269, 1179, 1138, 1091, 825, 677 cm$^{-1}$; MS (ESI) m/z 497.0-499.1 [M+H]⁺; UPLC purity 97%.

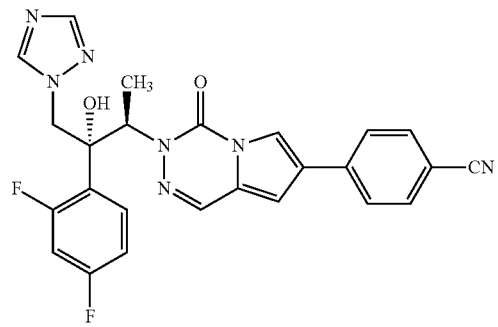

4-{3-[(1R,2R)-2-(2,4-Difluorophenyl)-2-hydroxy-1-methyl-3-(1,2,4-triazol-1-yl)propyl]-4-oxo-3,4-dihydro-pyrrolo[1,2-d][1,2,4]triazin-7-yl}benzonitrile (49)

According to the synthesis of 3-[(1R,2R)-2-(2,4-difluorophenyl)-2-hydroxy-1-methyl-3-(1,2,4-triazol-1-yl)propyl]-7-phenyl-3H-pyrrolo[1,2-d][1,2,4]triazin-4-one 47 starting from 7-bromo-3-[(1R,2R)-2-(2,4-difluorophenyl)-2-hydroxy-1-methyl-3-(1,2,4-triazol-1-yl)propyl]-3H-pyrrolo[1,2-d][1,2,4]triazin-4-one 45 (200 mg, 0.43 mmol) and 4-cyanobenzeneboronic acid (63 mg, 0.43 mmol). The residue was purified on silica gel column chromatography (methylene chloride/ethanol 99:1 and diethyl ether/ethyl acetate 80:20) to yield compound 49 as a light yellow powder (105 mg, 50%): $R_f$=0.23 (CH₂Cl₂/EtOH 98:2); mp: 201-202° C.; [α]$^{20}_D$=20.0 (c=0.1 in MeOH); $^1$H NMR (400 MHz, [D₆]DMSO): δ=1.24 (d, 3H, $^3J$=6.4 Hz), 4.54 (d, 1H, $^2J$=14.4 Hz), 4.93 (d, 1H, $^2J$=14.4 Hz), 5.65-5.72 (m, 2H), 6.97 (ddd, 1H, $^3J_{H-F}$=$^3J_{H-H}$=8.4 Hz, $^4J_{H-H}$=2.0 Hz), 7.25 (ddd, 1H, $^3J_{H-F}$=$^3J'_{H-F}$=9.6 Hz, $^4J_{H-H}$=2.0 Hz), 7.36 (m, 1H), 7.47 (s, 1H), 7.60 (s, 1H), 7.93 (d, 2H, $^3J_{H-H}$=8.4 Hz), 8.12 (d, 2H, $^3J_{H-H}$=8.4 Hz), 8.29 (s, 1H), 8.50 (s, 1H), 8.58 (s, 1H); $^{13}$C NMR (100 MHz, [D₆]DMSO): δ=14.1, 54.7, 54.9, 77.4, 103.9, 106.8, 109.7, 111.0, 115.5, 118.9, 124.0, 126.2, 126.7 (2C), 128.8, 130.1, 132.5, 132.9 (2C), 137.4, 144.7, 150.2, 157.4, 160.7 ppm; IR (KBr): ν=3447, 2221, 1699, 1500, 1388, 1293, 1138, 1047, 966, 804 cm$^{-1}$; MS (ESI) m/z 488.1 [M+H]⁺; UPLC purity 100%.

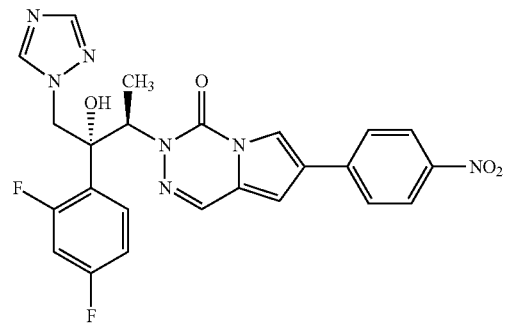 [SMILES: C[C@@H](n1ncc2cc(-c3ccc([N+](=O)[O-])cc3)cn2c1=O)[C@](O)(Cn1cncn1)c1ccc(F)cc1F]

3-[(1R,2R)-2-(2,4-Difluorophenyl)-2-hydroxy-1-methyl-3-(1,2,4-triazol-1-yl)propyl]-7-(4-nitrophenyl)-3H-pyrrolo[1,2-d][1,2,4]triazin-4-one (50)

According to the synthesis of 3-[(1R,2R)-2-(2,4-difluorophenyl)-2-hydroxy-1-methyl-3-(1,2,4-triazol-1-yl)propyl]-7-phenyl-3H-pyrrolo[1,2-d][1,2,4]triazin-4-one 47 starting from 7-bromo-3-[(1R,2R)-2-(2,4-difluorophenyl)-2-hydroxy-1-methyl-3-(1,2,4-triazol-1-yl)propyl]-3H-pyrrolo[1,2-d][1,2,4]triazin-4-one 45 (100 mg, 0.21 mmol) and 4-nitrobenzeneboronic acid (43 mg, 0.25 mmol). The residue was purified on silica gel column chromatography (petroleum ether/ethyl acetate 60:40) followed by C18 reverse-phase column chromatography (acetonitrile/water 50:50) to yield compound 50 as a brown powder (51 mg, 47%): $R_f$=0.25 (CH$_2$Cl$_2$/EtOH 98:2); mp: 130-131° C.; $[α]^{20}_D$=50.0 (c=0.1 in MeOH); NMR (400 MHz, [D$_6$]DMSO): δ=1.25 (d, 3H, $^3$J=6.8 Hz), 4.55 (d, 1H, $^2$J=14.4 Hz), 4.93 (d, 1H, $^2$J=14.4 Hz), 5.65-5.71 (m, 2H), 6.97 (ddd, 1H, $^3$J$_{H-F}$=$^3$J$_{H-H}$=8.4 Hz, $^4$J$_{H-H}$=2.4 Hz), 7.26 (ddd, 1H, $^3$J$_{H-F}$=$^3$J'$_{H-F}$=9.2 Hz, $^4$J$_{H-H}$=2.4 Hz), 7.36 (m, 1H), 7.51 (s, 1H), 7.60 (s, 1H), 8.21 (d, 2H, $^3$J$_{H-H}$=8.8 Hz), 8.29 (s, 1H), 8.32 (d, 2H, $^3$J$_{H-H}$=8.8 Hz), 8.53 (s, 1H), 8.64 (s, 1H); $^{13}$C NMR (100 MHz, [D$_6$]DMSO): δ=14.0, 54.7, 55.8, 77.4, 103.9, 107.0, 111.0, 115.9, 124.0, 124.2 (2C), 126.3, 126.9 (2C), 128.3, 130.1, 132.6, 139.4, 144.7 (2C), 146.4, 150.2, 158.6, 161.9 ppm; IR (KBr): ν=3448, 1701, 1509, 1342, 1212, 1132, 964, 852, 752 cm$^{-1}$; MS (ESI) m/z 508.0 [M+H]$^+$; UPLC purity 98%.

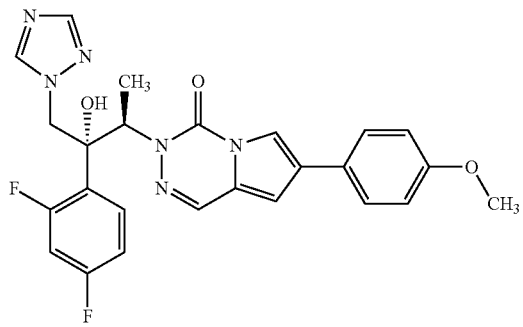 [SMILES: COc1ccc(-c2cc3cnn([C@H](C)[C@](O)(Cn4cncn4)c4ccc(F)cc4F)c(=O)n3c2)cc1]

residue was purified on silica gel column chromatography (diethyl ether and diethyl ether/ethyl acetate 90:10), then triturated in diisopropyl ether to yield after filtration compound 51 as a yellow powder (160 mg, 76%): $R_f$=0.29 (CH$_2$Cl$_2$/EtOH 98:2); mp: 172-173° C.; $[α]^{20}_D$=20.0 (c=0.1 in MeOH); NMR (400 MHz, [D$_6$]DMSO): δ=1.24 (d, 3H, $^3$J=6.8 Hz), 3.83 (s, 3H), 4.52 (d, 1H, $^2$J=14.4 Hz), 4.93 (d, 1H, $^2$J=14.4 Hz), 5.67-5.70 (m, 2H), 6.97 (ddd, 1H, $^3$J$_{H-F}$=$^3$J$_{H-H}$=8.4 Hz, $^4$J$_{H-H}$=2.4 Hz), 7.04 (d, 2H, $^3$J$_{H-H}$=8.8 Hz), 7.26 (ddd, 1H, $^3$J$_{H-F}$=$^3$J'$_{H-F}$=9.2 Hz, $^4$J$_{H-H}$=2.4 Hz), 7.31 (s, 1H), 7.36 (m, 1H), 7.60 (s, 1H), 7.82 (d, 2H, $^3$J$_{H-H}$=8.8 Hz), 8.28 (s, 1H), 8.30 (s, 1H), 8.46 (s, 1H); $^{13}$C NMR (100 MHz, [D$_6$]DMSO): δ=14.1, 22.8, 54.8, 55.2, 67.3, 77.4, 103.9, 106.5, 111.0, 113.0, 114.4, 124.1, 125.2, 125.8 (2C), 127.3 (2C), 130.1, 130.6, 132.4, 144.7, 150.2, 158.9, 158.7, 161.9 ppm; IR (KBr): ν=3447, 1700, 1616, 1500, 1428, 1407, 1387, 1298, 1250, 1180, 1134, 1029, 959, 808, 723 cm$^{-1}$; MS (ESI) m/z 493.1 [M+H]$^+$; UPLC purity 100%.

A/ Antifungal Activity

I. In Vitro Activities

I. 1. Fluconazole-Susceptible and -Resistant Strains of Candida Spp

Eight strains of Candida spp. with various azoles-susceptibilities were used:

One fluconazole-susceptible C. albicans strain: CAAL93

Two fluconazole-resistant C. albicans strains: CAAL111 (efflux pump) and CAAL117 (erg11 mutations+voriconazole-resistant)

five fluconazole-resistant Candida non albicans strains: C. krusei (CAKR7, CAKR8), C. glabrata (CAGL2), C. parapsilosis s.l. (CAPA1, CAPA2).

Antifungal susceptibility was evaluated with a spectrofluorimetric microdilution method. MIC was the concentration that was able to inhibit 50% of fluorescence measured in the control wells.

| | CAAL93 | CAAL111 | CAAL117 | CAKR7 | CAKR8 | CAGL2 | CAPA1 | CAPA2 |
|---|---|---|---|---|---|---|---|---|
| 27 | 0.014 ± 0.001 | | | | | | | |
| 44 | <0.001 | 0.48 ± 0.199 | 0.79 ± 0.092 | 0.625 ± 0.057 | 1.15 | 0.099 ± 0.004 | | |
| 29 | <0.001 | 0.005 ± 0.002 | | 1.28 ± 0.33 | 0.07 ± 0.02 | 0.15 ± 0.01 | 0.009 ± 0.003 | 0.007 ± 0.004 |
| 47 | <0.001 | 0.016 ± 0.001 | 0.014 ± 0.002 | 0.013 ± 0.001 | 0.014 | 0.008 ± 0.005 | | |
| 31 | <0.001 | | | | | | | |
| 48 | <0.001 | 0.018 ± 0.005 | 0.014 ± 0.001 | 0.019 ± 0.001 | 0.079 | 0.061 ± 0.008 | | |
| 35 | <0.001 | 0.007 ± 0.003 | | 0.18 ± 0.03 | 0.070 ± 0.01 | 0.20 ± 0.06 | 0.011 ± 0.003 | 0.004 ± 0.003 |
| 50 | <0.001 | 0.017 ± 0.007 | 0.018 ± 0.001 | 0.066 ± 0.009 | 0.039 ± 0.027 | 0.074 ± 0.038 | | |
| 34 | <0.001 | 0.003 ± 0.001 | | 0.45 ± 0.31 | 0.06 ± 0.01 | 0.64 ± 0.27 | 0.002 ± 0.001 | 0.002 ± 0.001 |
| 49 | <0.048 | | 0.016 ± 0.001 | 0.058 ± 0.009 | 0.101 ± 0.014 | 0.025 ± 0.010 | | |
| 51 | <0.001 | <0.001 | 0.018 ± 0.002 | 0.062 ± 0.032 | 0.081 ± 0.009 | 0.017 ± 0.003 | | |
| FLC | 0.036 ± 0.02 | >30 | >3 | >3 | >10 | 10.10 ± 0.61 | >30 | >30 |
| VOR | 0.005 ± 0.001 | 0.458 ± 0.196 | 1.1 ± 0.1 | 0.817 ± 0.007 | 0.24 ± 0.07 | 0.126 ± 0.003 | 0.95 ± 0.13 | 0.36 ± 0.001 |

3-[(1R,2R)-2-(2,4-Difluorophenyl)-2-hydroxy-1-methyl-3-(1,2,4-triazol-1-yl)propyl]-7-(4-methoxyphenyl)-3H-pyrrolo[1,2-d][1,2,4]triazin-4-one (51)

According to the synthesis of 3-[(1R,2R)-2-(2,4-difluorophenyl)-2-hydroxy-1-methyl-3-(1,2,4-triazol-1-yl)propyl]-7-phenyl-3H-pyrrolo[1,2-d][1,2,4]triazin-4-one 47 starting from 7-bromo-3-[(1R,2R)-2-(2,4-difluorophenyl)-2-hydroxy-1-methyl-3-(1,2,4-triazol-1-yl)propyl]-3H-pyrrolo[1,2-d][1,2,4]triazin-4-one 45 (200 mg, 0.43 mmol) and 4-methoxybenzeneboronic acid (65 mg, 0.43 mmol). The Globally, these results show that these compounds are more active than fluconazole (FLC) against Candida spp. strains (fluconazole-susceptible and resistant). They are at least as active as voriconazole (VOR).

Thus, these compounds are able to bypass the main known mechanisms of azole resistance (efflux, erg11 mutations).

It should be noticed that compounds 47, 48, 49, 50 and 51 are 100 fold more active than voriconazole against CAAL117.

I.2—Itraconazole-Susceptible and Resistant *Aspergillus fumigatus* Strains

Eleven strains of *A. fumigatus* with various itraconazole susceptibility were used:

Five susceptible strains: ASFU7, ASFU35A, ASFU38A, ASFU76 and ASFU78.

Six itraconazole-resistant strains: ASFU77 (erg11 mutation), ASFU13, ASFU17, ASFU19, ASFU20, ASFU23.

Antifungal susceptibility was evaluated with a spectrofluorimetric microdilution method. MIC was the concentration that was able to inhibit 80% of fluorescence measured in the control wells.

| | MIC values (µg/mL) | | | | |
|---|---|---|---|---|---|
| | ASFU76 | ASFU35A | ASFU38A | ASFU7 | ASFU78 |
| 27 | 6.76 ± 0.10 | 6.96 ± 1.49 | 23.03 ± 21.07 | 7.29 ± 0.22 | 6.03 ± 0.95 |
| 44 | 18.12 ± 10.10 | 21.37 ± 10.08 | 55.08 ± 9.96 | 24.31 ± 9.57 | 19.71 ± 12.94 |
| 29 | 6.66 ± 0.53 | 6.36 ± 1.42 | 6.86 ± 1.00 | 2.49 ± 0.13 | 5.93 ± 0.72 |
| 47 | 48.41 ± 7.95 | 41.33 ± 8.61 | 58.39 ± 15.65 | 44.06 ± 7.76 | 54.67 ± 12.10 |
| 31 | 5.70 ± 0.51 | 5.81 ± 0.50 | 5.59 ± 0.15 | 5.04 | 5.72 ± 0.39 |
| 48 | 6.21 ± 0.18 | 6.11 ± 0.85 | 6.64 ± 1.10 | 6.07 ± 0.05 | 6.26 ± 0.73 |
| 35 | 7.45 ± 1.00 | 6.71 ± 0.06 | 25.61 ± 24.84 | 2.52 ± 0.05 | 6.19 ± 0.80 |
| 50 | 8.23 ± 2.23 | 6.59 ± 0.04 | 8.86 | 8.31 ± 0.52 | 6.40 ± 1.07 |
| 34 | 6.44 ± 0.17 | 6.27 ± 0.30 | 12.62 ± 4.05 | 2.43 ± 0.19 | 5.98 ± 0.62 |
| 51 | 6.52 ± 0.16 | 6.08 ± 0.29 | 5.84 ± 0.20 | 2.21 ± 0.09 | 6.01 ± 0.48 |
| VOR | 0.64 ± 0.01 | 0.60 ± 0.08 | 0.75 ± 0.20 | 0.15 ± 0.001 | 0.59 ± 0.01 |
| ITRA | 0.50 ± 0.24 | 0.24 | 0.52 | 0.42 ± 0.04 | 0.31 |

Globally these molecules display promising biological results against all the ITRA and VOR-susceptible *A. fumigatus* isolates, with MIC values about 10 fold higher than the two references.

| | MIC values (µg/mL) | | | | | |
|---|---|---|---|---|---|---|
| | ASFU13 | ASFU17 | ASFU19 | ASFU77 | ASFU20 | ASFU23 |
| 27 | | | | 6.47 ± 0.03 | | |
| 44 | 4.06 | >38 | >38 | 52.75 ± 4.54 | 8.04 | 9.54 |
| 29 | | | | 28.23 ± 21.93 | | |
| 47 | | | | 64.80 ± 7.46 | | |
| 31 | | | | 5.99 ± 0.33 | | |
| 48 | 2.53 | >49 | >49 | 9.27 ± 1.05 | 2.51 | 2.48 |
| 35 | | | | 62.18 ± 2.92 | | |
| 50 | 3.08 | >50 | >50 | >100 | 21.33 | 42.98 |
| 34 | | | | 38.35 ± 13.13 | | |
| 51 | 2.03 | >49 | >49 | 6.60 ± 0.24 | 3.14 | 1.92 |
| VOR | 0.136 | 1.185 | 1.861 | 0.61 ± 0.04 | 0.178 | 0.097 |
| ITRA | >70 | >7 | >7 | >100 | >7 | >7 |

Compounds 27, 31, 48 and 51 are the most interesting against the ITRA-resistant *A. fumigatus* isolate carrying M220T mutation (ASFU77, MIC values in the micromolar range). In particularly, compounds 48 and 51 are also active against three other ITRA-resistant *A. fumigatus* isolates (ASFU13, ASFU20, ASFU23).

I.3—Cytotoxicity on HeLa Cells

Hela Human cell line was used in view to evaluate cytotoxicity. It was evaluated with a spectrofluorimetric microdilution method. $IC_{50}$ was the concentration that was able to inhibit 50% of fluorescence measured in the control wells.

Compounds 29 and 34 have an $IC_{50}$ of 25 µM.

Compounds 35 and 51 didn't show any cytotoxic effect at the higher concentration used (100 µM).

II. In Vivo Activities

Transiently neutropenic female Swiss mice were used for experiments on systemic candidiasis and invasive aspergillosis.

II.1—Murine Systemic Candidiasis

Mice were inoculated intravenously with a *Candida albicans* strain (CAAL93). Treatment was administrated once a day (10 mg/kg per os) for 5 days. Mice survival was observed for 28 days (except compound 51, 14 days). Fungal burden of the kidney was evaluated in dead animals during the experimentation or in animals sacrificed at the end of the experimentation.

Figure 2:
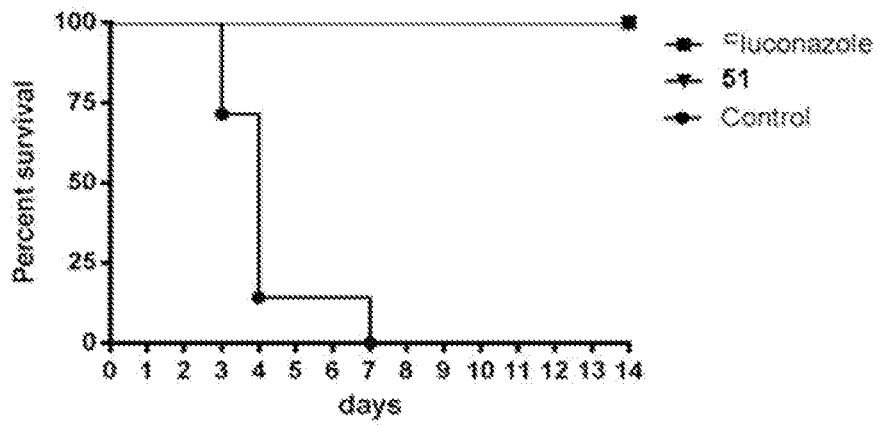

Results (% survival) are illustrated in FIGS. 1 and 2.

Analysis of the survival curves showed that groups treated with compounds 29, 34, 35 and 51 have a significant longer survival compared with the non-treated group (p<0.05).

Moreover, compounds 34 and 35 are significantly more efficient than FLC.

Fungal burden of the kidney was significantly decreased when mice were treated with compounds 29, 34 and 35 (p<0.05). Activity was significantly higher when compared to FLC (p<0.05). Compound 51 is the most active (p<0.001).

Figure 3:
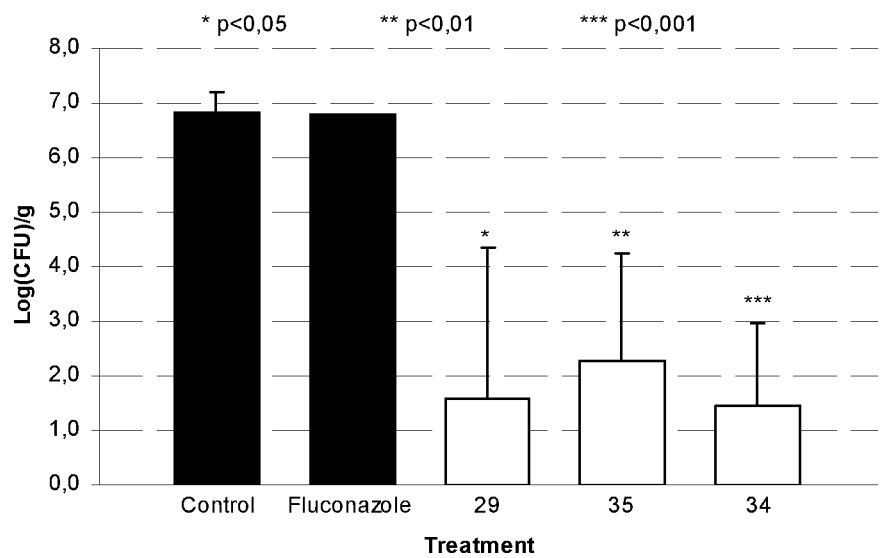
Figure 4:
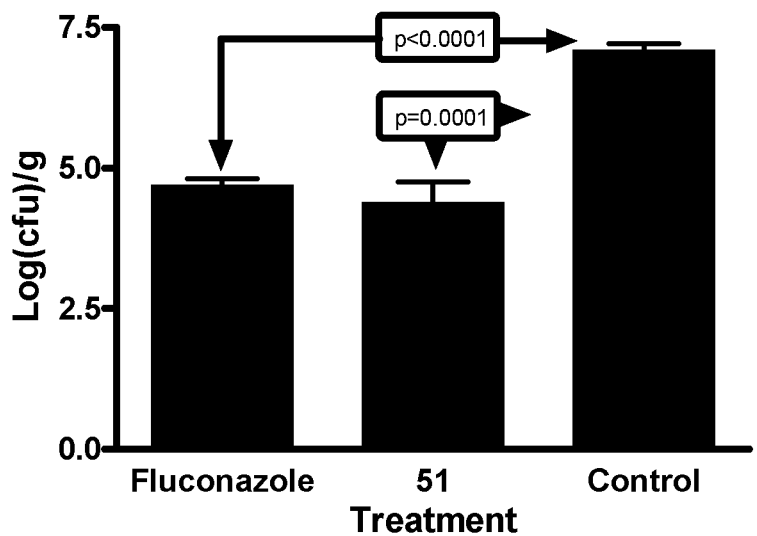

Results are illustrated in FIGS. 3 and 4.

II.2—Murine Invasive Aspergillosis

Mice were inoculated intravenously with *Aspergillus fumigatus* (ASFU7) spores.

Treatment was administrated once a day (10 mg/kg per os) for 5 days. Mice survival was observed for 14 days. Fungal burden of the kidney was evaluated in dead animals during the experimentation or in animals sacrificed at the end of the experimentation.

Figure 5:
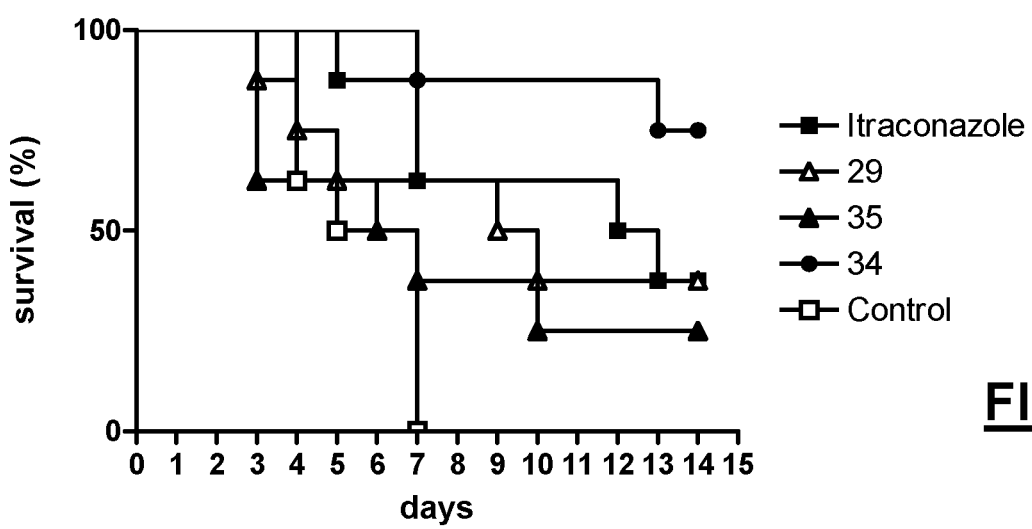
FIG. 5 represents the survival rate of swiss mice following inoculation with the ASFU7 strain and administration of compounds 29, 34, 35.
Figure 6:
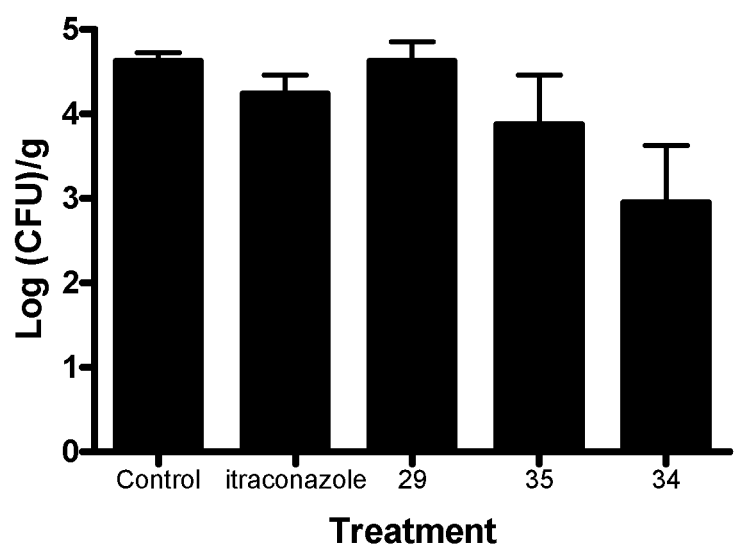
FIG. 6 represents the fungal load in swiss mice following inoculation with the ASFU7 strain and administration of compounds 29, 34, 35.

Analysis of survival curve (FIG. 5) show that treated animals with ITRA or compound 34 did survive significantly longer (p<0.01). Compound 34 is significantly more active than compounds 29 and 35 (p<0.05) (see FIG. 6).

Compound 51 was not evaluated.

Fungal burden of the kidney was significantly reduced when mice were treated with ITRA or compound 34 (p<0.05).

II.3—Acute Oral Toxicity Study in Rats

This study has been performed for compound 51 by CiToxLAB Hungary Ltd.

Summary

The single-dose oral toxicity of compound 51 was performed according to the acute toxic class method (OECD 423 and Commission Regulation (EC) No 440/2008 of 30 May 2008, B.1.Tris) in CRL:(WI) rats.

Two groups of three female CRL:(WI) rats were treated with the test item at a dose level of 300 mg/kg bw (Group 1 and Group 2).

A single oral treatment was carried out by gavage for each animal after an overnight food withdrawal. Food was made available again 3 hours after the treatment. The test item was administered formulated in DMSO at a concentration of 30 mg/mL at a dose volume of 10 mL/kg bw.

Initially, three females (Group 1) were treated at a dose level of 300 mg/kg bw. As no mortality was observed, a confirmatory group (Group 2) was treated at the same dose level. No mortality was observed in the confirmatory group.

For full classification, treatment at 2000 mg/kg is required, but due to lack of availability of test item from the Sponsor, no further testing with a higher dose level was possible. Hence classification as $LD_{50}$>300 mg/kg is possible.

Clinical observations were performed at 30 minutes, 1, 2, 3, 4 and 6 hours after dosing and daily for 14 days thereafter. Body weight was measured on days −1, 0 and 7 and before necropsy. All animals were subjected to a necropsy and a macroscopic examination Results Mortality Compound 51 did not cause mortality at a dose level of 300 mg/kg bw.

Clinical Observations

Treatment with compound 51 caused hunched back and slightly decreased activity in all the experimental animals at the dose level of 300 mg/kg bw. All animals were symptom free from the next day after treatment.

Body Weight and Body Weight Gain

Body weight gains of compound 51 treated animals during the study showed no indication of a test item-related effect.

Macroscopic Findings

There was no evidence of the macroscopic observations at a dose level of 300 mg/kg bw.

CONCLUSION

Under the conditions of this study, the acute oral $LD_{50}$ value of the test item compound 51 was found to be above 300 mg/kg bw in female CRL:(WI) rats. According the GHS criteria, compound 51 can be ranked as "Category 4" for acute oral exposure.

B/ Anti-Trypanosomatidae Activity

Compounds were evaluated on the promastigote stage of a *Leishmania mexicana* strain using a spectrofluorimetric microdilution method. Inhibitory concentration 50 ($IC_{50}$) was the concentration that inhibited 50% of the control growth.

|  | *L. mexicana* ($IC_{50}$ μM) |
| --- | --- |
| 27 | >100 |
| 28 | >100 |
| 29 | 2.8 ± 0.3 |
| 30 | 8.1 ± 1.6 |
| 34 | 2.8 ± 0.2 |
| 35 | 11.4 ± 1.5 |
| Itraconazole | 2.5 ± 0.7 |
| Pentamidine | 0.34 ± 0.03 |

Compounds 29, 30, 34 and 35 were effective against the promastigote stage of *L. Mexicana*.

The invention claimed is:

1. A compound of formula (I):

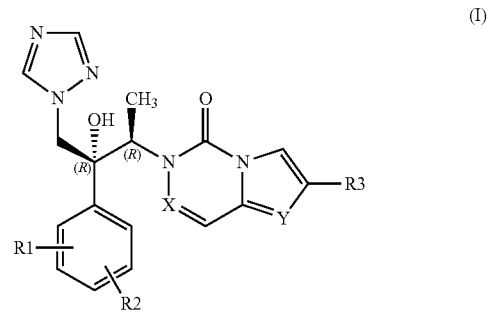

wherein X is selected from the group consisting of CH and N;
Y is selected from the group consisting of CH and N;
R1 and R2, identical or different are independently chosen from the group consisting of Halogen atoms,
R3 is selected from the group consisting of H; (C1-C6) alkyl; CN; COO(C1-C6)alkyl; OH, halogen atoms, O(C1-C6)alkyl, $NO_2$, perhalogeno(C1-C6)alkyl, CO(C1-C6)alkyl, $CONH_2$, CONH(C1-C6)alkyl, CON[(C1-C6)alkyl]2, $(CH_2)_n$NRR; 5 to 10 membered aryl groups optionally substituted by one or more identical or different groups chosen from: halogen atoms, perhalogeno(C1-C6)alkyl, CN, $NO_2$, O(C1-C6)Alkyl, OH, (C1-C6)alkyl, CO(C1-C6)alkyl, COO(C1-C6) alkyl, COOH, CONRR', 5 to 10 membered heteroaryl groups comprising one, two or three heteroatoms chosen from O, N and S;
n is 0 or 1;
R represents a H atom or a group COR";
R' represents a H atom or is selected from the group consisting of (C1-C6)alkyl,
R" is selected from the group consisting of (C1-C6)alkyl, (C2-C6)alkenyl, and pharmaceutically acceptable salts thereof.

2. The compound according to claim 1, wherein X is CH and Y is N.

3. The compound according to claim 1, wherein X is N; and Y is CH.

4. The compound according to claim 1, wherein R1 and R2 are located in ortho and para positions of the phenyl ring.

5. The compound according to claim 1, wherein R3 is selected from the group consisting of 5 to 10 membered aryl groups optionally substituted by one or more identical or different groups chosen from: halogen atoms, perhalogeno (C1-C6)alkyl, CN, $NO_2$, O(C1-C6)Alkyl, and 5 to 10 membered heteroaryl groups comprising one, two or three heteroatoms chosen from O, N and S.

6. The compound according to claim 1 selected from the group consisting of:
- 6-[(1R,2R)-2-(2,4-Difluorophenyl)-2-hydroxy-1-methyl-3-(1H-1,2,4-triazol-1-yl)propyl]imidazo[1,2-c]pyrimidin-5-one,
- 6-[(1R,2R)-2-(2,4-Difluorophenyl)-2-hydroxy-1-methyl-3-(1H-1,2,4-triazol-1-yl)propyl]-2-methylimidazo[1,2-c]pyrimidin-5-one,
- 6-[(1R,2R)-2-(2,4-Difluorophenyl)-2-hydroxy-1-methyl-3-(1H-1,2,4-triazol-1-yl)propyl]-2-phenylimidazo[1,2-c]pyrimidin-5-one,
- 6-[(1R,2R)-2-(2,4-Difluorophenyl)-2-hydroxy-1-methyl-3-(1H-1,2,4-triazol-1-yl)propyl]-2-(4-fluorophenyl)imidazo[1,2-c]pyrimidin-5-one,
- 6-[(1R,2R)-2-(2,4-Difluorophenyl)-2-hydroxy-1-methyl-3-(1H-1,2,4-triazol-1-yl)propyl]-2-(4-chlorophenyl)imidazo[1,2-c]pyrimidin-5-one,
- 6-[(1R,2R)-2-(2,4-Difluorophenyl)-2-hydroxy-1-methyl-3-(1H-1,2,4-triazol-1-yl)propyl]-2-(4-bromophenyl)imidazo[1,2-c]pyrimidin-5-one,
- 6-[(1R,2R)-2-(2,4-Difluorophenyl)-2-hydroxy-1-methyl-3-(1H-1,2,4-triazol-1-yl)propyl]-2-[(4-trifluoromethyl)phenyl]imidazo[1,2-c]pyrimidin-5-one,
- 6-[(1R,2R)-2-(2,4-Difluorophenyl)-2-hydroxy-1-methyl-3-(1H-1,2,4-triazol-1-yl)propyl]-2-(4-cyanophenyl)imidazo[1,2-c]pyrimidin-5-one,
- 6-[(1R,2R)-2-(2,4-Difluorophenyl)-2-hydroxy-1-methyl-3-(1H-1,2,4-triazol-1-yl)propyl]-2-(4-nitrophenyl)imidazo[1,2-c]pyrimidin-5-one,
- 6-[(1R,2R)-2-(2,4-Difluorophenyl)-2-hydroxy-1-methyl-3-(1H-1,2,4-triazol-1-yl)propyl]-2-(thiazol-2-yl)imidazo[1,2-c]pyrimidin-5-one,
- Ethyl-6-[(1R,2R)-2-(2,4-difluorophenyl)-2-hydroxy-1-methyl-3-(1H-1,2,4-triazol-1-yl)propyl]-5-oxo-imidazo[1,2-c]pyrimidine-2-carboxylate,
- 6-[(1R,2R)-2-(2,4-Difluorophenyl)-2-hydroxy-1-methyl-3-(1H-1,2,4-triazol-1-yl)propyl]-5-oxo-imidazo[1,2-c]pyrimidine-2-carbonitrile,
- 3-[(1R,2R)-2-(2,4-Difluorophenyl)-2-hydroxy-1-methyl-3-(1,2,4-triazol-1-yl)propyl]-3H-pyrrolo[1,2-d][1,2,4]triazin-4-one,
- 7-Bromo-3-[(1R,2R)-2-(2,4-difluorophenyl)-2-hydroxy-1-methyl-3-(1,2,4-triazol-1-yl)propyl]-3H-pyrrolo[1,2-d][1,2,4]triazin-4-one,
- 3-[(1R,2R)-2-(2,4-Difluorophenyl)-2-hydroxy-1-methyl-3-(1,2,4-triazol-1-yl)propyl]-4-oxo-3,4-dihydro-pyrrolo[1,2-d][1,2,4]triazine-7-carbonitrile,
- 3-[(1R,2R)-2-(2,4-Difluorophenyl)-2-hydroxy-1-methyl-3-(1,2,4-triazol-1-yl)propyl]-7-phenyl-3H-pyrrolo[1,2-d][1,2,4]triazin-4-one,
- 7-(4-Chlorophenyl)-3-[(1R,2R)-2-(2,4-difluorophenyl)-2-hydroxy-1-methyl-3-(1,2,4-triazol-1-yl)propyl]-3H-pyrrolo[1,2-d][1,2,4]triazin-4-one,
- 4-{3-[(1R,2R)-2-(2,4-Difluorophenyl)-2-hydroxy-1-methyl-3-(1,2,4-triazol-1-yl)propyl]-4-oxo-3,4-dihydro-pyrrolo[1,2-d][1,2,4]triazin-7-yl}benzonitrile,
- 3-[(1R,2R)-2-(2,4-Difluorophenyl)-2-hydroxy-1-methyl-3-(1,2,4-triazol-1-yl)propyl]-7-(4-nitrophenyl)-3H-pyrrolo[1,2-d][1,2,4]triazin-4-one,
- 3-[(1R,2R)-2-(2,4-Difluorophenyl)-2-hydroxy-1-methyl-3-(1,2,4-triazol-1-yl)propyl]-7-(4-methoxyphenyl)-3H-pyrrolo[1,2-d][1,2,4]triazin-4-one, and pharmaceutically acceptable salts thereof.

7. A process of preparation of a compound according to claim 1 comprising the step of coupling a compound of formula (II) with a compound of formula (III):

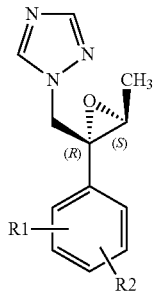

(II)

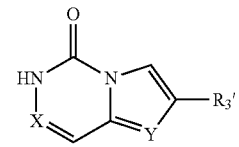

(III)

where $R_3'$ is a R3 group or a leaving group;
optionally followed by converting the compound so obtained by the coupling of compounds (II) and (III) into a compound (I) with the desired R3 group.

8. The process according to claim 7 wherein the compound (III) is obtained by a process comprising the step of reacting a compound (IV) with a compound (V):

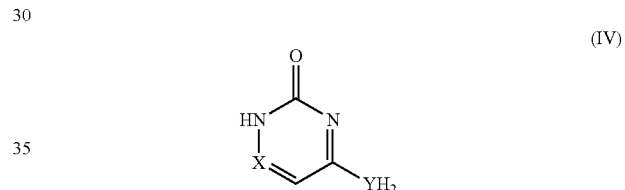

(IV)

(V)

where Hal represents a halogen atom.

9. The process according to claim 7, wherein the compound of formula (III) is obtained from a compound of formula (VI)

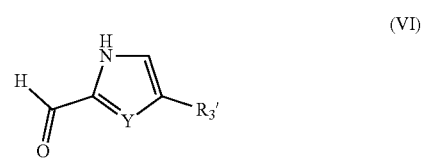

(VI)

with ethylcarbazate ($H_2NNHCOOEt$) followed by the addition of a base.

10. The process according to claim 7 further comprising the additional step of isolating the compound obtained by the process according to claim 7.

11. A pharmaceutical composition comprising a compound of formula (I) according to claim 1 with at least one pharmaceutically acceptable excipient.

12. A method for the treatment of fungal infections comprising administering a compound of formula (I) according to claim 1.

13. A method for the treatment of parasitic infectious diseases due to Trypanosomatidae comprising administering a compound of formula (I) according to claim 1.

* * * * *